(12) United States Patent
Moon et al.

(10) Patent No.: US 10,105,198 B2
(45) Date of Patent: Oct. 23, 2018

(54) DENTAL MEMBRANE

(71) Applicant: OSSTEMIMPLANT CO., LTD., Seoul (KR)

(72) Inventors: Jong Hoon Moon, Busan (KR); Si Young Jung, Busan (KR); Tae Gwan Eom, Busan (KR); Kyoo Ok Choi, Seoul (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 240 days.

(21) Appl. No.: 14/368,037

(22) PCT Filed: Dec. 24, 2012

(86) PCT No.: PCT/KR2012/011387
§ 371 (c)(1),
(2) Date: Jun. 23, 2014

(87) PCT Pub. No.: WO2013/095077
PCT Pub. Date: Jun. 27, 2013

(65) Prior Publication Data
US 2014/0349251 A1 Nov. 27, 2014

(30) Foreign Application Priority Data

Dec. 23, 2011 (KR) .......... 10-2011-0141350
Jan. 12, 2012 (KR) .......... 10-2012-0003854

(51) Int. Cl.
*A61C 8/00* (2006.01)
*A61C 8/02* (2006.01)

(52) U.S. Cl.
CPC .......... *A61C 8/0031* (2013.01); *A61C 8/0006* (2013.01); *A61C 8/008* (2013.01); *A61C 8/0022* (2013.01)

(58) Field of Classification Search
CPC ..... A61C 8/006; A61C 8/0031; A61C 8/0022; A61C 8/0006; A61F 2/2803; A61F 2/2846
(Continued)

(56) References Cited

U.S. PATENT DOCUMENTS 5,432,917 A   7/1995 Parikh
5,433,607 A * 7/1995 Schmid ................ A61C 8/0031
                                                          433/173
(Continued)

FOREIGN PATENT DOCUMENTS

CA      2 235 705 A1   10/1999
CN      1181228 A       5/1998
(Continued)

OTHER PUBLICATIONS

European Search Report dated Sep. 8, 2015, for European Patent Application No. 12860152.3. (7 pages).
(Continued)

*Primary Examiner* — Nicholas Lucchesi
(74) *Attorney, Agent, or Firm* — Fitch, Even, Tabin & Flannery LLP

(57) ABSTRACT

A dental membrane disposed in a deficient region of an alveolar bone to form a space for regeneration of the alveolar bone or to surround a bone graft, wherein the dental membrane is fixed by an insert inserted and fixed in the alveolar bone and a cover member combined to the insert, the dental membrane including: an upper portion surrounding a top surface of the deficient region of the alveolar bone; and a side bending portion bended downward from the upper portion and surrounding a side surface of the deficient region of the alveolar bone, wherein the upper portion includes: a combined portion combined to the insert and the cover
(Continued)

member to be fixed; and a protruding portion extending and protruding upward from the combined portion.

22 Claims, 35 Drawing Sheets

(58) Field of Classification Search
USPC .... 433/172, 173, 174, 175, 176; 623/17, 18, 623/19
See application file for complete search history.

(56) References Cited

U.S. PATENT DOCUMENTS

| | | | |
|---|---|---|---|
| 5,769,637 A * | 6/1998 | Morgan | A61B 17/8071 433/176 |
| 5,944,526 A | 8/1999 | Liu | |
| 5,976,140 A | 11/1999 | Haas | |
| 6,171,106 B1 | 1/2001 | Kaneko et al. | |
| 6,238,214 B1 | 5/2001 | Robinson | |
| 6,332,777 B1 | 12/2001 | Sutter | |
| 6,394,807 B2 | 5/2002 | Robinson | |
| 8,888,485 B2 * | 11/2014 | Ali | A61C 8/0027 433/173 |
| 9,339,354 B2 * | 5/2016 | Moon | A61F 2/2803 |
| 2003/0232308 A1 * | 12/2003 | Simmons, Jr. | A61C 8/0031 433/173 |
| 2005/0192675 A1 | 9/2005 | Robinson | |
| 2007/0269483 A1 * | 11/2007 | Elia | A61C 8/00 424/424 |
| 2009/0317765 A1 * | 12/2009 | Dacremont | A61C 8/0031 433/174 |
| 2010/0112522 A1 * | 5/2010 | Kwon | A61C 8/0031 433/174 |
| 2013/0288199 A1 * | 10/2013 | Wen | A61C 19/063 433/173 |

FOREIGN PATENT DOCUMENTS

| | | |
|---|---|---|
| EP | 2 737 871 A2 | 6/2014 |
| EP | 2737871 A4 * | 5/2015 ........... A61F 2/2803 |
| JP | H5-505952 | 9/1993 |
| JP | H6-83713 A | 3/1994 |
| JP | H7-23982 A | 1/1995 |
| JP | 2895457 B2 | 3/1999 |
| JP | 2000-83970 A | 3/2000 |
| JP | 2000-116674 A | 4/2000 |
| JP | 2002-224141 A | 8/2002 |
| JP | 2002-369830 A | 12/2002 |
| JP | 3414757 B2 | 4/2003 |
| JP | 2010-524556 A | 7/2010 |
| JP | 2010-284248 A | 12/2010 |
| JP | 4698033 B | 3/2011 |
| JP | 2011-212209 A | 10/2011 |
| KR | 10-2010-0025369 A | 3/2010 |
| KR | 10-2010-0102403 A | 9/2010 |
| KR | 10-1053052 B1 | 8/2011 |
| KR | 10-1061758 B1 | 9/2011 |
| WO | 2005/092236 A1 | 10/2005 |
| WO | 2005/105164 A1 | 11/2005 |
| WO | WO 2006051401 A2 * | 5/2006 ........... A61C 8/0006 |

OTHER PUBLICATIONS

Taiwanese Office Action dated May 15, 2015, for Taiwanese Patent Application No. 101149624.
International Search Report from the International Bureau of WIPO for International Application No. PCT/KR2012/011387 dated Mar. 27, 2013 and English translation of the same (5 pages).
Written Opinion from the International Bureau of WIPO for International Application No. PCT/KR2012/011387 dated Mar. 27, 2013 and English translation of the same (8 pages).
Notice of Allowance issued in corresponding Korean Patent Application No. 10-2011-0141350 dated Apr. 20, 2012 and English translation of the same (7 pages).
Japanese Office Action dated Jun. 3, 2015, for Japanese Patent Application No. 2014-548689. (Japanese only).
Chinese Office Action dated May 23, 2016, for Chinese Patent Application No. 201280070577.9. (11 pages).

* cited by examiner

DENTAL MEMBRANE

CROSS-REFERENCE TO RELATED APPLICATIONS

This application is a National Phase Patent Application of International Patent Application Number PCT/KR2012/011387, filed on Dec. 24, 2012, which claims priority of Korean Patent Application Number 10-2011-0141350, filed Dec. 23, 2011, and Korean Patent Application Number 10-2012-0003854, filed Jan. 12, 2012, which are hereby incorporated herein by reference in their entirety.

TECHNICAL FIELD

The present invention relates to a dental membrane, and more particularly, to a dental membrane capable of obtaining stability of a surgical procedure by minimizing a space between gingivae.

BACKGROUND ART

Generally, when a tooth falls out, a denture is put in a mouth or a bridge procedure for covering a space of the fallen tooth with a metal or the like is performed, by using surrounding teeth as supports. However, according to such surgical procedures, a denture and a bridged artificial tooth are weak for chewing and may adversely affect surrounding teeth. Thus, an implant procedure has appeared as one of developed dental procedures. According to the implant procedure, an artificial tooth root is formed in an alveolar bone and is combined to an artificial tooth that is a final prosthetic appliance manufactured similar to an actual tooth, and thus a patient obtains an effect of using an actual tooth.

According to the implant procedure, an implant groove is formed on an alveolar bone where a tooth has fallen out by using a tool, such as a drill, so as to implant a fixture, and tapping is performed as a selective operation for the fixture to be strongly implanted in the implant groove. After implanting the fixture in the implant groove, a cover screw is locked to the fixture and gums are sutured to prevent impurities from penetrating into the fixture, thereby completing a primary surgery. Then, a secondary surgery is performed after about 3 to 6 months by cutting the sutured gums to remove the cover screw from the fixture, considering a type of abutment to be locked, and then selecting and locking a healing abutment to the fixture. Here, the healing abutment is locked so that the gums are neatly formed on the fixture before locking the abutment to the fixture. After the gums are formed suitably for locking the abutment after about 2 to 3 weeks, the healing abutment is removed and then the abutment is combined to the fixture. Then, the implant procedure is completed by combining a final prosthetic appliance having a shape of a natural tooth to a top of the abutment.

According to such a general implant procedure, when a part of the alveolar bone is lost and it is difficult to sufficiently support the fixture only by using the remaining alveolar bone, a surgical procedure of filling a bone graft in the lost part such that the bone graft operates as a new alveolar bone is additionally performed. In other words, the surgical procedure of generating the lost part of the alveolar bone is performed, which is called guided bone regeneration (GBR). In order to perform the GBR, first, the fixture is inserted into the alveolar bone and the bone graft, such as an artificial bone or autogenous bone, is filled in the lost part. Then, the fixture is covered by a dental membrane so that the filled bone graft maintains a required shape. Next, the dental membrane is fixed to a required location by using a predetermined cover member.

Such a conventional technology is disclosed in U.S. Pat. No. 6,171,106 about "Cover Screw for Dental Implant", wherein FIG. 1 is a representative drawing. Here, as shown in FIG. 1, a male screw 3a of a main body 3 is screwed to a threaded hole 1a of an implant fixture 1 implanted to an alveolar bone B, and a barrier membrane 5 is mounted on a face 3b to cover a partial top of the alveolar bone B. A male screw 4c of a membrane fixing screw 4 is screwed to a threaded hole 3c of the main body 3, wherein the barrier membrane 5 is inserted and fixed therebetween. Meanwhile, a gingival G is disposed on the barrier membrane 5 to cover the barrier membrane 5 so as to prevent external impurities or pollutants from penetrating into the barrier membrane 5 during GBR.

However, a dental membrane according to such a conventional technology has the following problems.

First, a fixing screw is disposed on the dental membrane according to the conventional technology, and a space is formed on the top of the dental membrane due to the fixing screw. The space may have a size corresponding to a height of the fixing screw. For example, when the fixing screw is thick, the space may be big, and when the fixing screw is thin, the space may be small. If the space is generated as such, undesired impurities or foreign matters may be filled in the space, and thus an inside of a gingiva may be contaminated. Such contamination interferes with osseointegration, thereby increasing a bone regeneration time or causing osteolysis if worse.

In addition, according to the dental membrane of the conventional technology, it is not easy to form an alveolar process that bulges in an arch shape around an implanted tooth. Generally, an alveolar process bulges around a tooth and commonly exists in a general tooth. A gingiva having a similar shape as the alveolar process is formed on the alveolar process, and the gingiva formed around an artificial tooth in 3-dimensions arouses an aesthetic sense of a viewer. Meanwhile, the alveolar process has a bulging shape, but since a conventional dental membrane has a simple flat or bended shape, it is not easy to form the alveolar process.

On the other hand, it was easy to make a space in a bone deficient region, i.e., increase a bone horizontally and vertically, by using titanium, which is a nonabsorbent material compared to other materials. However, in an anterior region where an aesthetic sense is required, not only is the increasing of the bone important, but the shape of the increased bone is also important. In other words, for the aesthetic sense of the anterior region, a gingival papilla (a bulging portion formed between teeth or around a tooth) needs to be formed, but it is difficult for an operator to form the gingival papilla via bending and trimming at the spot of dental treatment by using the conventional dental membrane.

In detail, in order to obtain a satisfactory bone increasing effect while realizing a gingival papilla, an additional procedure of grinding or trimming an alveolar bone is required. However, such an additional procedure is not only difficult to be performed, but also burdens a patient and an operator in terms of time and expense.

SUMMARY OF THE INVENTION

The present invention provides an alveolar bone that is easily regenerated by decreasing a space between a cover member and a gingiva. In other words, the alveolar bone is formed by inserting a bone graft into the space.

The present invention also provides an alveolar process having an arch shape, which is easily formed, so as to increase convenience of a surgical procedure.

The present invention also provides a dental membrane, wherein a papilla is formed while an alveolar bone is regenerated.

In particular, the present invention also provides a dental membrane, wherein a papilla is easily formed without having to perform an additional procedure by an operator on the spot, such as bending and trimming the dental membrane or grinding or trimming an alveolar bone.

According to an aspect of the present invention, there is provided a dental membrane disposed in a deficient region of an alveolar bone to form a space for regeneration of the alveolar bone or to surround a bone graft, wherein the dental membrane is fixed by an insert inserted and fixed in the alveolar bone and a cover member combined to the insert, the dental membrane including: an upper portion surrounding a top surface of the deficient region of the alveolar bone; and a side bending portion bended downward from the upper portion and surrounding a side surface of the deficient region of the alveolar bone, wherein the upper portion includes: a combined portion combined to the insert and the cover member, wherein the combined portion is fixed to the insert and the cover member; and a protruding portion extending and protruding upward from the combined portion.

The combined portion may be ring shaped, have a center, and have a through hole at the center.

The protruding portion may surround at least a part of a side surface of the cover member.

The protruding portion may have a shape corresponding to an outer shape of the cover member.

The protruding portion may contact a side surface of the cover member.

The protruding portion may be spaced apart from the side surface of the cover member.

An uppermost end of the protruding portion may be disposed on a same location as a top surface of the cover member.

The protruding portion may protrude from the combined portion in a range from 0.1 mm to 5 mm.

The protruding portion may have a cylindrical shape.

At least one hole may be formed in the protruding portion.

The protruding portion may include: a first extending portion connected to the combined portion and extending upward; and a second extending portion horizontally extending from the first extending portion.

The dental membrane may include two side bending portions that are respectively disposed on two sides of the upper portion.

According to another aspect of the present invention, there is provided a dental membrane disposed in a deficient region of an alveolar bone to form a space for regeneration of the alveolar bone or to surround a bone graft, wherein the dental membrane is fixed by an insert inserted and fixed in the alveolar bone and a cover member combined to the insert, the dental membrane including: an upper portion surrounding a top surface of the deficient region and including a combined portion fixed by contacting the insert and a protruding portion extending and protruding upward from the combined portion; and a side bending portion bending downward from the upper portion.

The combined portion may be ring shaped, have a center, and have a through hole at the center.

The protruding portion may surround at least a part of a side surface of the cover member.

The protruding portion may have a shape corresponding to an outer shape of the cover member.

The protruding portion may contact a side surface of the cover member.

The protruding portion may be spaced apart from the side surface of the cover member.

An uppermost end of the protruding portion may be disposed on a same location as a top surface of the cover member.

The protruding portion may protrude from the combined portion in a range from 0.1 mm to 5 mm.

At least one hole may be formed in the protruding portion.

The protruding portion may include: a first extending portion connected to the combined portion and extending upward; and a second extending portion horizontally extending from the first extending portion.

The dental membrane may include two side extending portions that are respectively disposed on two sides of the upper portion.

The side extending portion may be bendable downward from the upper portion.

According to another aspect of the present invention, there is provided a dental membrane disposed in a deficient region of an alveolar bone to form a space for regeneration of the alveolar bone or to surround a bone graft, wherein the dental membrane is fixed by an implant insert inserted and fixed in the alveolar bone, the dental membrane including: an upper portion surrounding a top surface of the deficient region of the alveolar bone, wherein the bone graft is filled in the deficient region of the alveolar bone; and a side bending portion bended downward from the upper portion and surrounding a side surface of the deficient region of the alveolar bone, wherein the bone graft is filled in the deficient region of the alveolar bone, wherein the upper portion includes: a center portion disposed at a location corresponding to a location where the implant insert is inserted, and having a center hole combined to the implant insert; and a papilla forming portion disposed to surround at least a part of the center portion, wherein the papilla forming portion protrudes upward from the center portion to induce formation of a papilla that convexly protrudes upward and is formed on the alveolar bone when the alveolar bone is being regenerated.

The papilla forming portion may have a ring shape surrounding the center portion.

The papilla forming portion may locally protrude at any one of a tongue side, a lip side, and an adjacent tooth side.

A vertical distance from the center portion to an uppermost end of the papilla forming portion may be from 0.1 mm to 3 mm.

The papilla forming portion may be spaced apart from the center hole by a predetermined distance.

The upper portion may further include an upper extending portion bending downward by extending in a direction opposite to an extending direction of the side bending portion.

The upper portion may further include an upper wing portion bending downward by extending from two sides of the upper portion.

The side bending portion may further include a side wing portion bending inward by extending from two sides of the side bending portion.

A plurality of minute holes may be formed in the side wing portion.

The side bending portion may further include a side extending portion bending inward by extending downward from a bottom of the side bending portion.

According to another aspect of the present invention, there is provided a dental membrane disposed in a deficient region of an alveolar bone to form a space for regeneration of the alveolar bone or to surround a bone graft, wherein the dental membrane is fixed by a plurality of fixing screws disposed on an edge, the dental membrane including: an upper portion surrounding a top surface of the deficient region of the alveolar bone, wherein the bone graft is filled in the deficient region of the alveolar bone; and a side bending portion bended downward from the upper portion and surrounding a side surface of the deficient region of the alveolar bone, wherein the bone graft is filled in the deficient region of the alveolar bone, wherein the upper portion includes: a center portion where a plurality of minute holes are formed; and a papilla forming portion disposed to surround at least a part of the center portion, wherein the papilla forming portion protrudes upward from the center portion to induce formation of a papilla that convexly protrudes upward and is formed on the alveolar bone when the alveolar bone is being regenerated.

The papilla forming portion may have a ring shape surrounding the center portion.

The papilla forming portion may locally protrude at any one of a tongue side, a lip side, and an adjacent tooth side.

A vertical distance from the center portion to an uppermost end of the papilla forming portion may be from 0.1 mm to 3 mm.

According to another aspect of the present invention, there is provided a dental membrane disposed in a deficient region of an alveolar bone to form a space for regeneration of the alveolar bone or to surround a bone graft, wherein the dental membrane is fixed by an implant insert inserted and fixed in the alveolar bone, the dental membrane including: an upper portion surrounding a top surface of the deficient region of the alveolar bone, wherein the bone graft is filled in the deficient region of the alveolar bone; and a horizontal extending portion horizontally extending from the upper portion, wherein the upper portion includes: a center portion disposed at a location corresponding to a location where the implant insert is inserted, and having a center hole combined to the implant insert; and a papilla forming portion disposed to surround at least a part of the center portion, wherein the papilla forming portion protrudes upward from the center portion to induce formation of a papilla that convexly protrudes upward and is formed on the alveolar bone when the alveolar bone is being regenerated.

The papilla forming portion may have a ring shape surrounding the center portion.

The papilla forming portion may locally protrude at any one of a tongue side, a lip side, and an adjacent tooth side.

A vertical distance from the center portion to an uppermost end of the papilla forming portion may be from 0.1 mm to 3 mm.

The papilla forming portion may be spaced apart from the center hole by a predetermined distance.

The horizontal extending portion may be formed to a curved shape according to a shape of the alveolar bone when the alveolar bone is being regenerated.

According to another aspect of the present invention, there is provided a dental membrane disposed in a deficient region of an alveolar bone to form a space for regeneration of the alveolar bone or to surround a bone graft, wherein the dental membrane is fixed by a plurality of fixing screws disposed on an edge, the dental membrane including: an upper portion surrounding a top surface of the deficient region of the alveolar bone, wherein the bone graft is filled in the deficient region of the alveolar bone; and a horizontal extending portion horizontally extending from the upper portion, wherein the upper portion includes: a center portion having a plurality of minute holes; and a papilla forming portion disposed to surround at least a part of the center portion, wherein the papilla forming portion protrudes upward from the center portion to induce formation of a papilla that convexly protrudes upward and is formed on the alveolar bone when the alveolar bone is being regenerated.

The papilla forming portion may have a ring shape surrounding the center portion.

The papilla forming portion may locally protrude at any one of a tongue side, a lip side, and an adjacent tooth side.

A vertical distance from the center portion to an uppermost end of the papilla forming portion may be from 0.1 mm to 3 mm.

The horizontal extending portion may be formed to a curved shape according to a shape of the alveolar bone when the alveolar bone is being regenerated.

In a dental membrane according to the present embodiment, a protruding portion protrudes to surround a cover member, and thus a space between a gingiva and the dental membrane may be reduced even when the gingiva covers the dental membrane.

Also, since a dental membrane according to the present invention includes a papilla forming portion capable of forming a papilla on an alveolar bone to be regenerated, the papilla may be easily formed.

In addition, according to the present invention, an operator does not need to bend and trim a dental membrane at the spot of the dental treatment, and a papilla may be easily formed without having to grind or cut a generated alveolar bone. Thus, convenience of a surgical procedure may be increased.

DETAILED DESCRIPTION OF THE PREFERRED EMBODIMENTS

Figure 1:
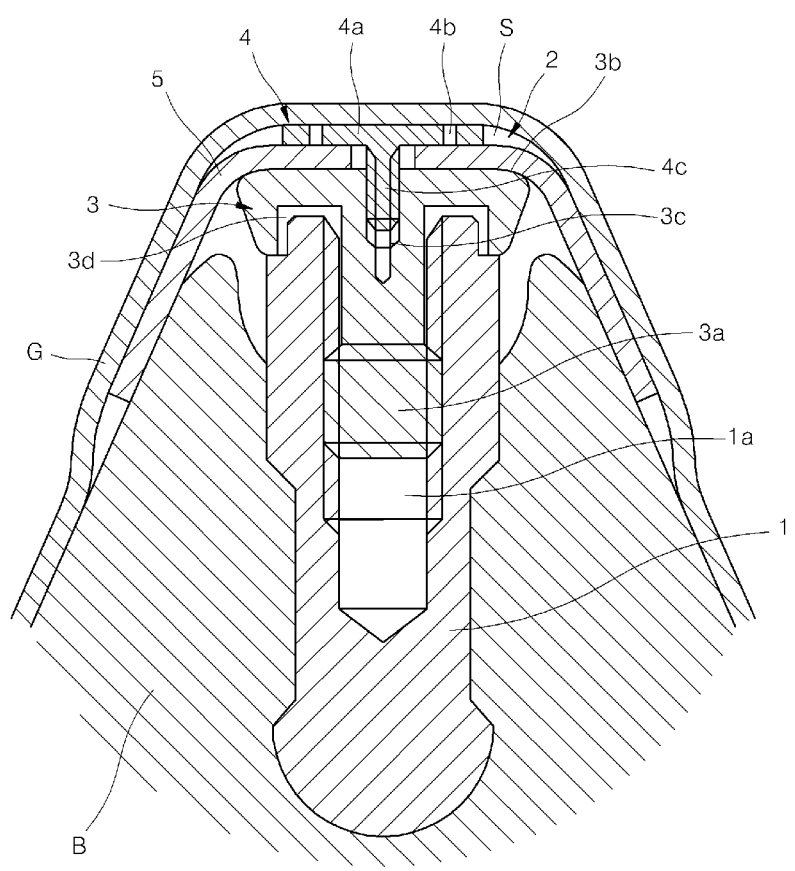
FIG. 1 is a view of a dental membrane according to a conventional technology.
Figure 2:
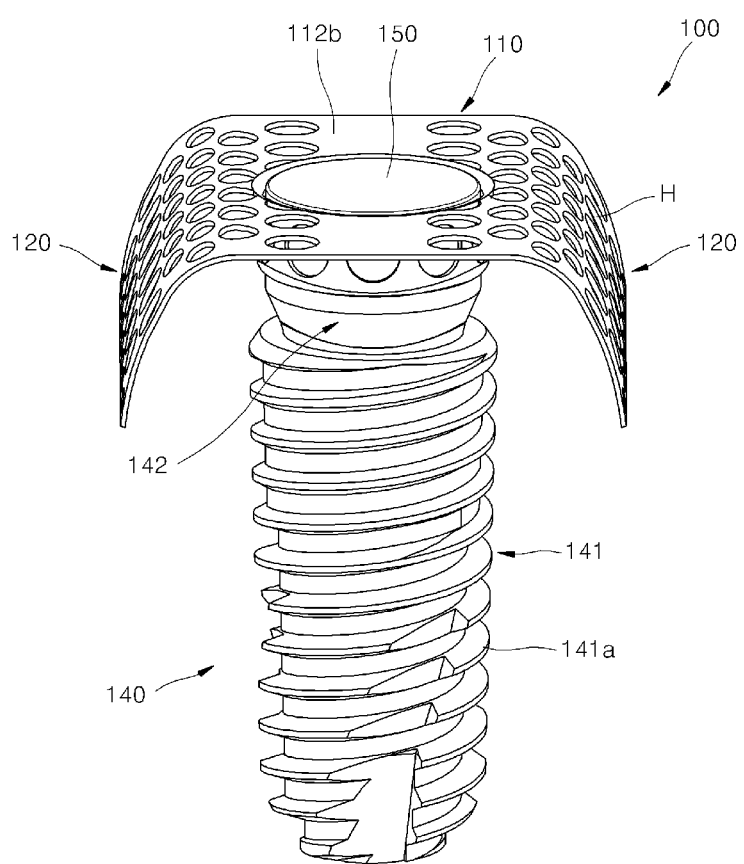
FIG. 2 is a perspective view of a dental membrane combined with an insert and a cover member, according to an embodiment of the present invention.
Figure 3:
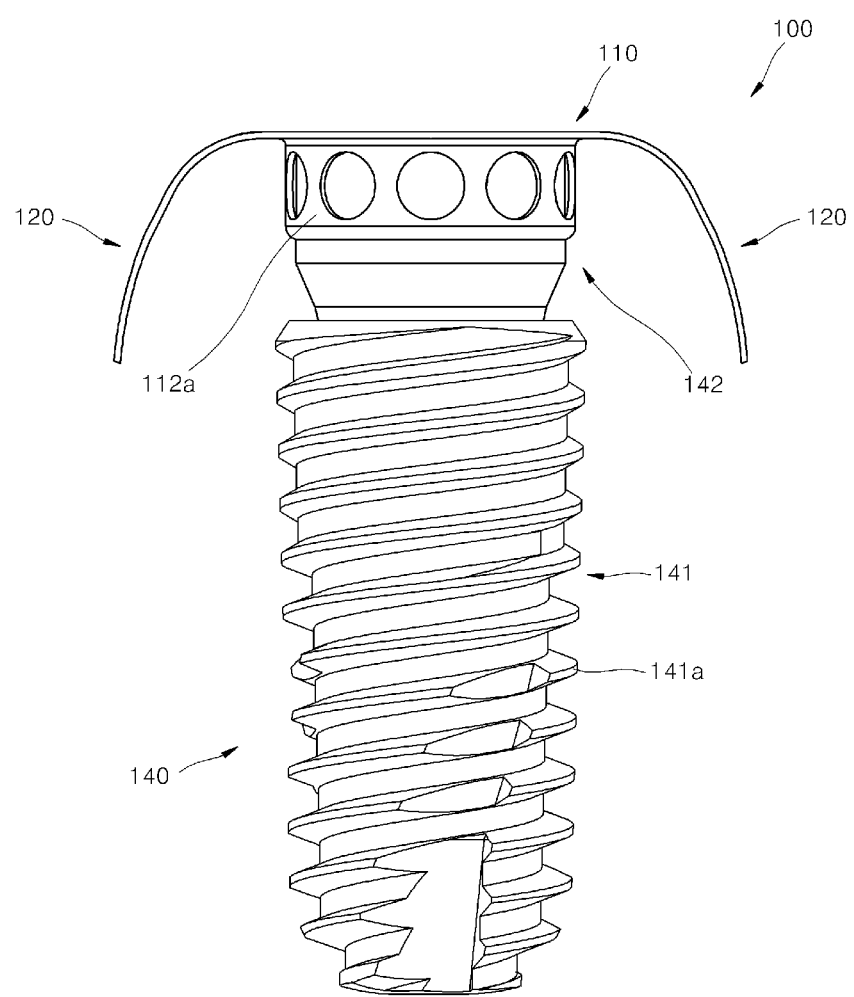
FIG. 3 is a lateral view of FIG. 2.
Figure 4:
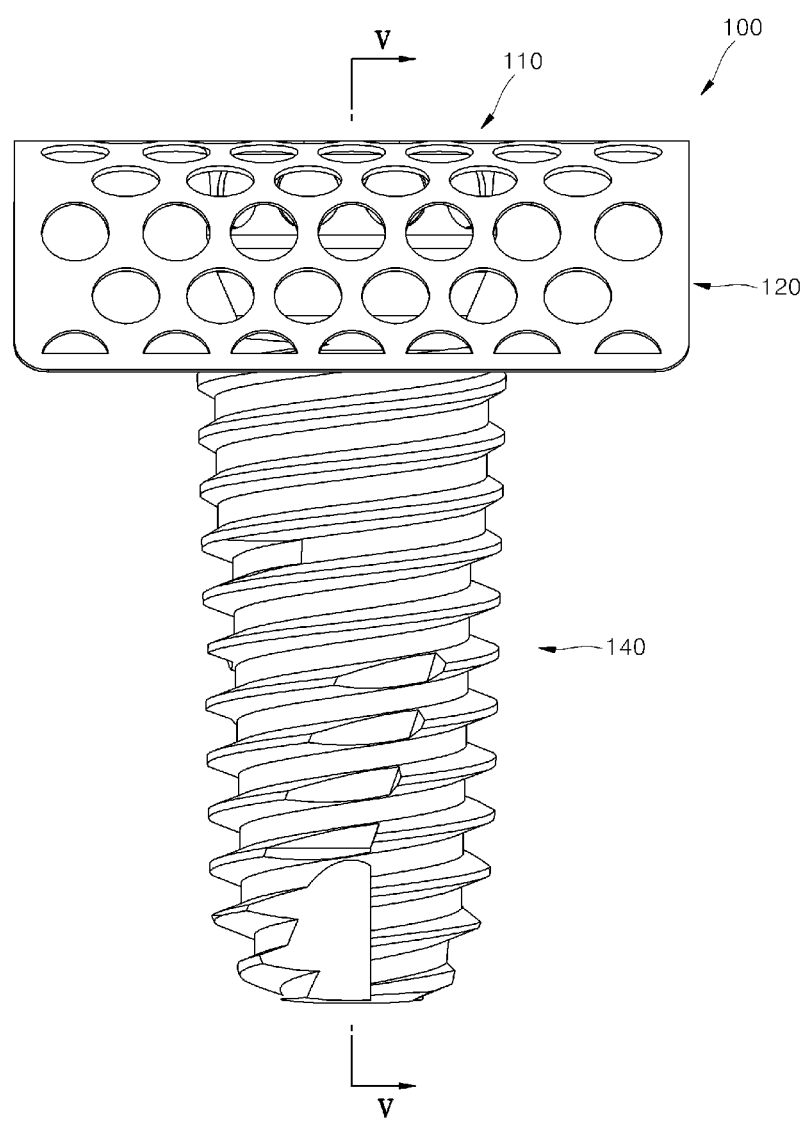
FIG. 4 is a rear view of FIG. 3.

Hereinafter, a dental membrane according to one or more embodiments of the present invention will be described in detail with reference to accompanying drawings.

A dental membrane 100 according to an embodiment of the present invention is disposed in a deficient region of an alveolar bone B to form a space for the alveolar bone B to be regenerated or surround a bone graft BG, and thus is a shielding film preventing the surrounded bone graft BG from deviating from the dental membrane 100. A location of the dental membrane 100 may be fixed by an insert 140 inserted and fixed in the alveolar bone B, and a cover member 150 combined to the insert 140. In detail, since the dental membrane 100 is inserted into a human body, the dental membrane 100 may be formed of a material harmless to the human body. Also, the dental membrane 100 may be somewhat elastic so as to be transformable according to a shape of the alveolar bone B. Meanwhile, since a plurality of holes H are formed in the dental membrane 100, blood may circulate through the dental membrane 100 during bone grafting, thereby facilitating the bone grafting.

The dental membrane 100 may have a flat shape and may be bent by an operator at the spot of the dental treatment if required, but alternatively, the dental membrane 100 may be pre-formed in three-dimensions according to the shape of the alveolar bone B by a manufacturer and provided to the operator.

The dental membrane 100 may include an upper portion 110 and a side bending portion 120.

The upper portion 110 surrounds a top surface of the deficient region of the alveolar bone B. In detail, the upper portion 110 covers a deficient region where the bone graft BG is filled in the deficient region, while surrounding a top surface of the deficient region.

The upper portion 110 includes a combined portion 111 and a protruding portion 112.

A location of the combined portion 111 is fixed by being combined to the insert 140 and the cover member 150. The combined portion 111 has a ring shape in an overall flat plate shape, and has a through hole 111a at the center through which the insert 140 or the cover member 150 is inserted and penetrated. A top surface of the combined portion 111 may contact a bottom surface of the cover member 150, and a bottom surface of the combined portion 111 may contact a top surface of the insert 140.

The protruding portion 112 protrudes upward from the combined portion 111. In detail, the protruding portion 112 surrounds at least a part of the cover member 150 and may have a shape corresponding to an outer shape of the cover member 150. For example, in the current embodiment, since the cover member 150 has a circular plate shape, the protruding portion 112 may have a cylindrical shape. Here, the protruding portion 112 may closely contact a side surface of the cover member 150. When the protruding portion 112 closely contacts the side surface of the cover member 150 as such, a space may be reduced, thereby preventing pollutants filled in the space. Alternatively, the protruding portion 112 may be spaced apart from the cover member 150 by a predetermined distance. In this case, a space to which a removing tool for removing the cover member 150 is to be combined may be prepared.

Meanwhile, an uppermost end of the protruding portion 112 may be disposed lower than or on a same location as a top surface of the cover member 150, and in detail, may be disposed at a same height as the top surface of the cover member 150. When the uppermost end of the protruding portion 112 is on the same height as the cover member 150 as such, a space between the dental membrane 100 and a gingiva G may be decreased.

In detail, the protruding portion 112 may protrude from the combined portion 111 in a range from 0.1 mm to 5 mm. When a height of the protruding portion 112 is lower than 0.1 mm, the space is increased, and when the height of the protruding portion 112 is higher than 5 mm, the protruding portion 112 may protrude further upward than the cover member 150.

The protruding portion 112 includes a first extending portion 112a having a cylindrical shape and connected to the combined portion 111, and a second extending portion 112b extending horizontally from the first extending portion 112a. Here, the second extending portion 112b is connected to the side bending portion 120.

At least one hole H may be formed in the protruding portion 112.

The side bending portion 120 bends downward from the upper portion 110 while surrounding a side surface of the deficient region of the alveolar bone B, and has a plurality of holes H. The side bending portion 120 bends from the upper portion 110 in a gradual round shape while a bottom of the side bending portion 120 is retracted inward, thereby preventing the bone graft BG therein from flowing out as much as possible. The side bending portion 120 may be disposed on each side of the upper portion 110. However, alternatively, the side bending portion 120 may be disposed on only one side of the upper portion 110.

Meanwhile, reference numerals 140 and 150 respectively denote an insert and a cover member. A location of the insert 140 is fixed by being inserted into the alveolar bone B, and the insert 140 may include a fixture 141 and an abutment 142 combined to the fixture 141. The fixture 141 has a cylindrical shape in overall, wherein a screw thread 141*a* is formed on an outer circumference of the fixture 141 to be combined to the alveolar bone B, and a blind hole 141*b* is formed downward from a top of the fixture 141.

The abutment 142 is inserted into the blind hole 141*b* of the fixture 141, and protrudes from the fixture 141 such that an additional space in which the bone graft BG is to be filed in is obtained by the protruding height. A combining projection 142*a* protruding upward is prepared on a top of the abutment 142. A male screw thread is formed on the combining projection 142*a*.

The cover member 150 is combined to the abutment 142, and in detail, a groove 151 to be combined to the combining projection 142*a* is formed at a bottom of the cover member 150. The dental membrane 100 according to the current embodiment is fixed between the cover member 150 and the abutment 142.

The dental membrane 100 according to the current embodiment has the following effects.

Figure 5:
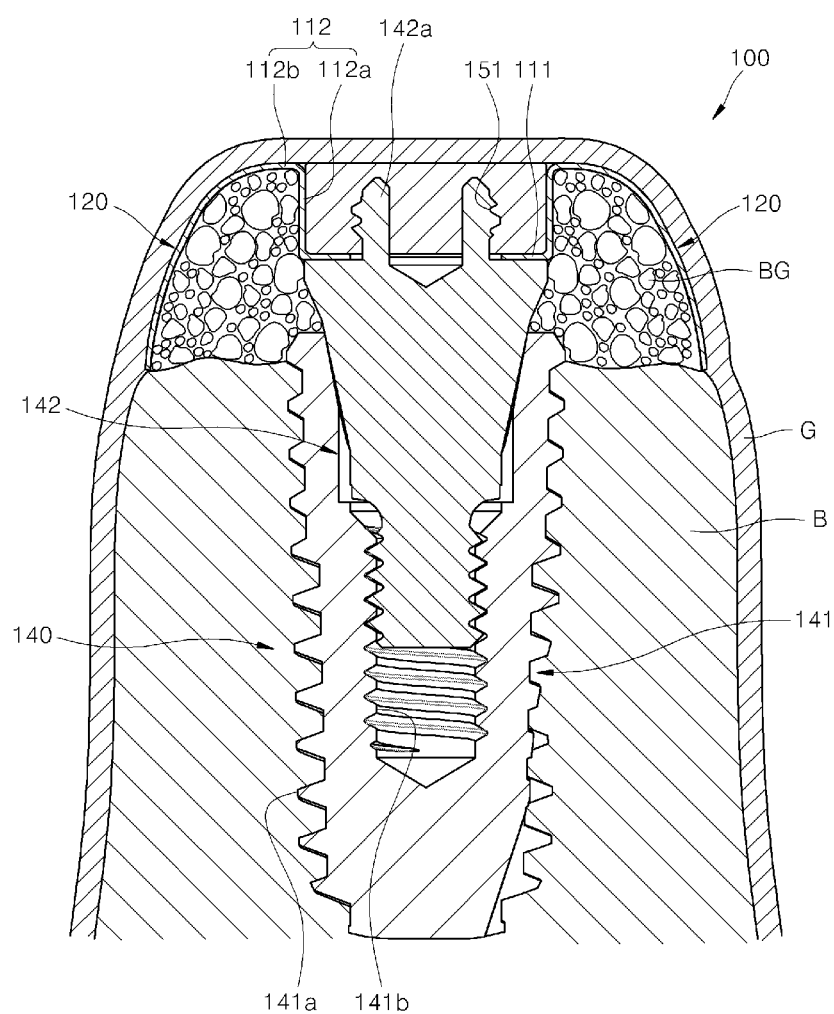
FIG. 5 is a cross-sectional view taken along a line V-V of FIG. 4, wherein the dental membrane is implanted in an alveolar bone.
Figure 6:
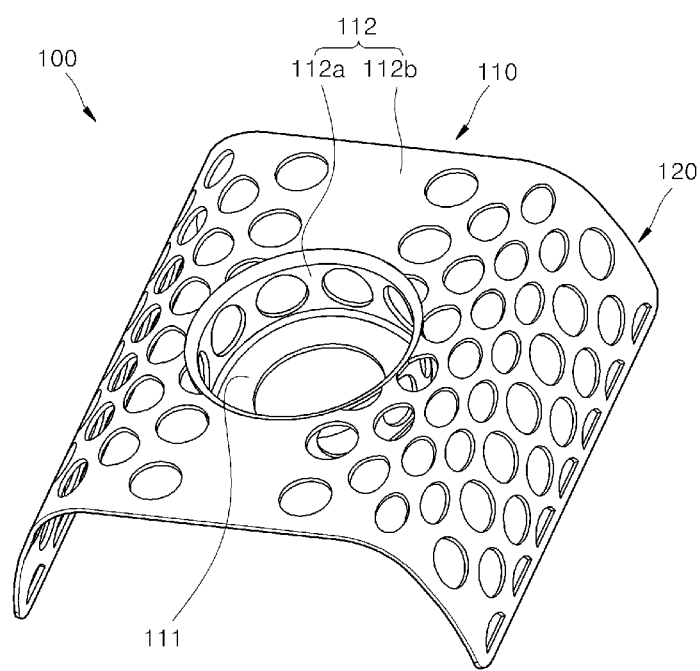
FIG. 6 is a perspective view of the dental membrane of FIG. 2.
Figure 7:
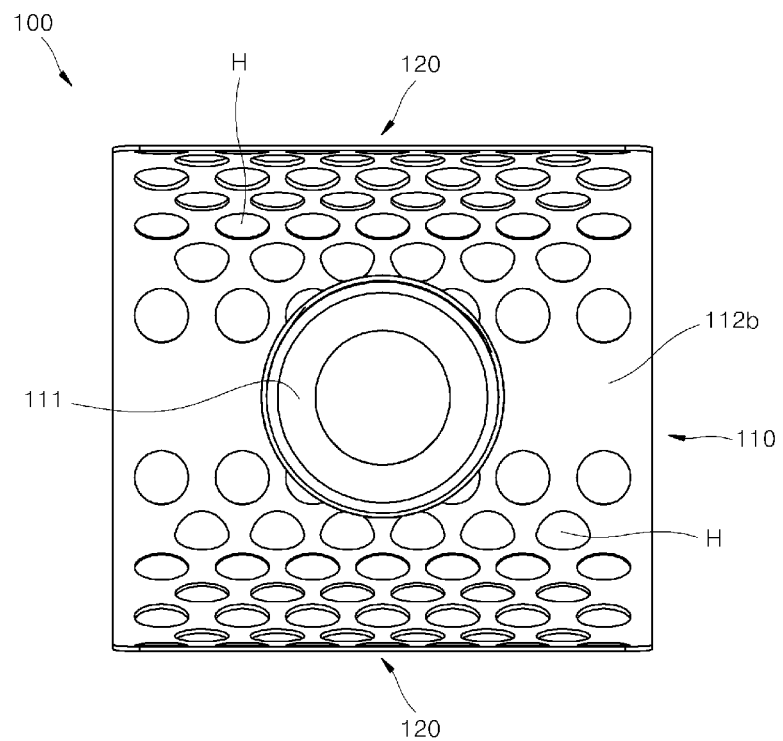
FIG. 7 is a plan view of FIG. 6.
Figure 8:
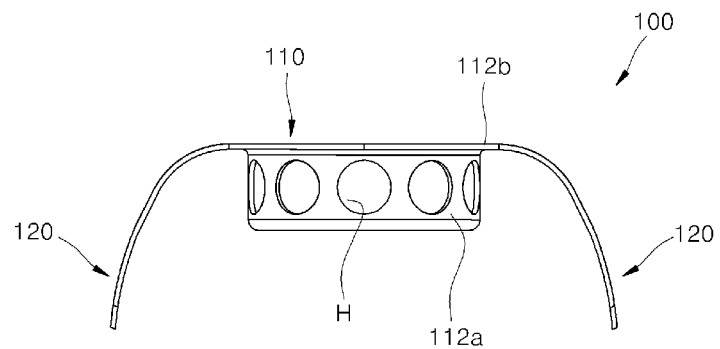
FIG. 8 is a lateral view of FIG. 6.

First, referring to FIG. 5 illustrating the dental membrane 100 according to the current embodiment being implanted in the alveolar bone B, the dental membrane 100 whose location is fixed by the insert 140 and the cover member 150 combined to the deficient region of the alveolar bone B is disposed to cover the bone graft BG. Here, the combined portion 111 of the upper portion 110 is interlocked and combined by the insert 140 and the cover member 150, and the protruding portion 112 is disposed to surround the cover member 150. As such, when the dental membrane 100 protrudes while surrounding the cover member 150, a space between the gingiva G and the dental membrane 100 may be decreased even when the gingiva G covers the dental membrane 100. In particular, since the uppermost end of the protruding portion 112 is at the same height as the top surface of the cover member 150, a space therebetween may be reduced, and thus foreign matters or pollutants may be prevented from being filled in the space.

Also, an amount of the alveolar bone B generated as the bone graft BG is filled in a space newly generated by the protruding portion 112 may be increased. According to the increased amount of the alveolar bone B, the fixture 141 may be more strongly fixed in the alveolar bone B in comparison to related technology. Also, by deleting a part of the alveolar bone B, an alveolar process having an arch shape may be easily formed. For example, a desired alveolar process may be easily obtained, without having to additionally perform osteoanagenesis, by deleting the alveolar bone B prepared in the space formed by the protruding portion 112 to a desired shape.

The dental membrane 100 according to the current embodiment may be modified as follows.

Figure 9:
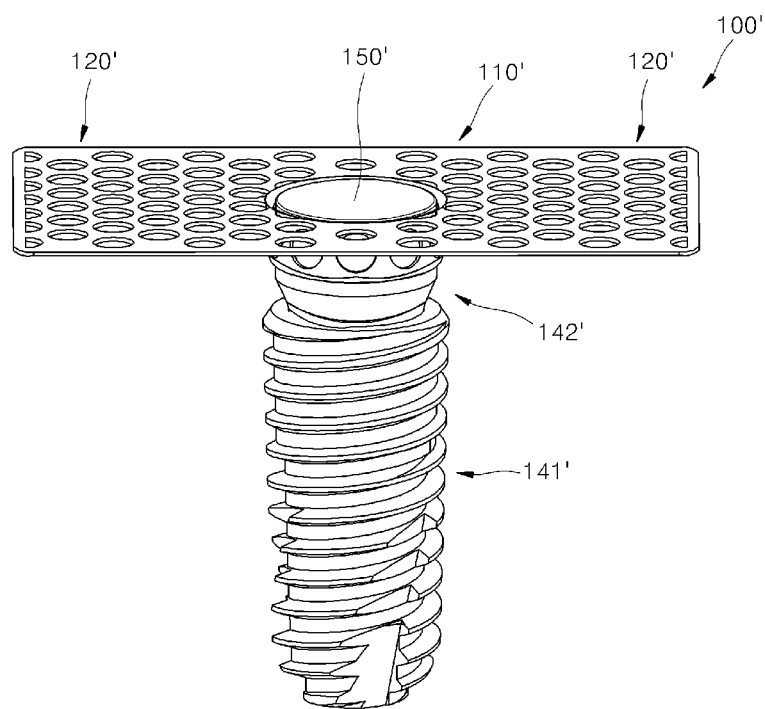
FIG. 9 is a perspective view of a dental membrane combined with an insert and a cover member, according to another embodiment of the present invention.
Figure 10:
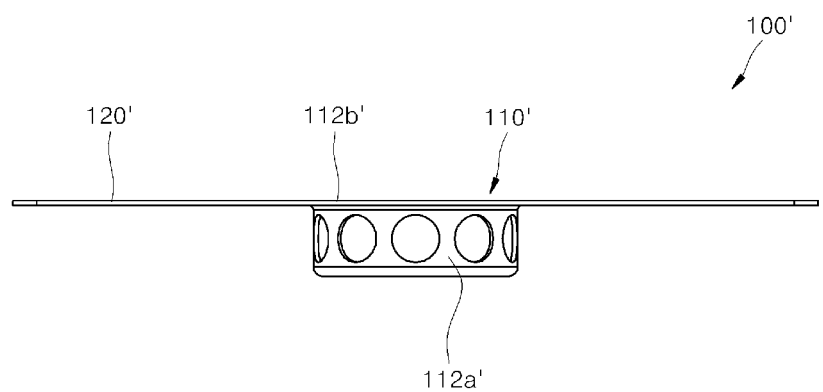
FIG. 10 is a lateral view of the dental membrane of FIG. 9.

In the above embodiment, the side bending portion 120 around the upper portion 110 bends downward, but alternatively, a side extending portion 120' may be disposed around an upper portion 110' as shown in FIGS. 9 and 10. The side extending portion 120' horizontally extends from the upper portion 110', wherein a pair of the side extending portions 120' are disposed around the upper portion 110', and at least one hole is formed on each side extending portion 120'.

The side extending portion 120' may itself be used in the alveolar bone B, but if required, the side extending portion 120' may be bent according to the alveolar bone B by the operator. Meanwhile, an insert including a fixture 141' and an abutment 142', a cover member 150', a first extending portion 112*a*', and a second extending portion 112*b*' of FIG. 9 or 10 have the same shape as those described above, and thus details thereof are not repeated here.

Figure 11:
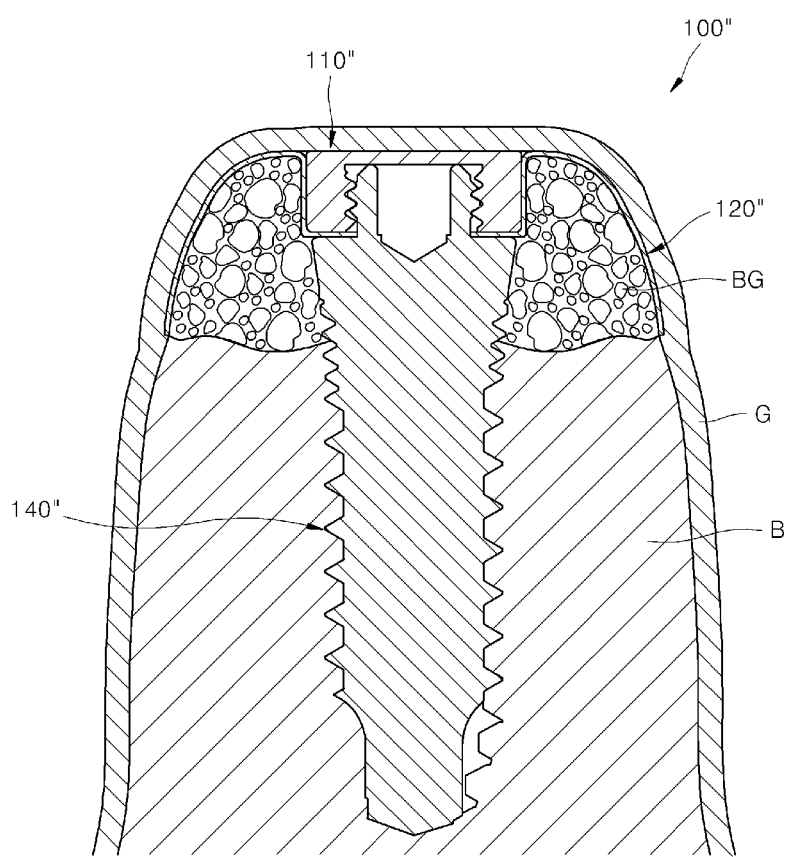
FIG. 11 is a view of a dental membrane according to an embodiment of the present invention.

Also in the above embodiment, the insert 140 includes the fixture 141 and the abutment 142 combined to the fixture 141, but the structure of the insert 140 is not limited thereto. For example, as shown in FIG. 11, an insert 140" may only include an abutment integrated fixture, without an individually separated abutment. Here, a cover member 150" is combined to the abutment integrated fixture of the insert 140", thereby fixing a location of a dental membrane 100". An upper portion 110" and a side bending portion 120" of the dental membrane 100" have the same shape as those described above, and thus details thereof are not repeated here.

Alternatively, an insert may only include a fixture. For example, the insert may only include a fixture shown in FIG. 5, and a cover member may be directly combined to the fixture.

Accordingly, in overall, an insert may include a combination of a fixture and an abutment (a shape of FIG. 5), only a fixture (a shape of FIG. 5 excluding the abutment), or an abutment integrated fixture (a shape of FIG. 11).

In the above embodiment, a protruding portion has a shape corresponding to a cover member, but alternatively, the protruding portion may recede away from the cover member upward from a combined portion (i.e., a distance between the protruding portion and the cover member is increased). For example, when the cover member has a circular plate shape, the protruding portion may have a conical shape. In this case, an alveolar process may be easily formed. In other words, an amount of an alveolar bone to be deleted to form the alveolar process from the alveolar bone may be reduced.

In particular, the protruding portion may be designed to have a shape corresponding to the alveolar process to be regenerated. In this case, the alveolar process may have been formed without having to delete the alveolar bone.

Also in the above embodiment, a protruding portion has a cylindrical shape, but alternatively, the protruding portion may be disposed in at least one of a tongue side, an adjacent tooth side, and a lip side of an alveolar bone.

Also, in the above embodiment, a dental membrane is disposed between an insert and a cover member, but alternatively, a groove may be prepared in the insert along a circumferential direction and the dental membrane may be inserted and combined to the groove. Here, a protruding portion may have a shape corresponding to an upper portion of the insert protruding from the dental membrane.

A dental membrane having a papilla forming portion inducing forming of a papilla will now be described.

A dental membrane 10 according to an embodiment of the present invention induces regeneration of an alveolar bone 80 by surrounding a bone graft 82 filled in a deficient region of the alveolar bone 80. In detail, the dental membrane 10 covers the bone graft 82, such as autogenous bone or artificial bone, filled in the deficient region of the alveolar bone 80, thereby preventing the bone graft 82 from deviating from the deficient region during osteoanagenesis and stably inducing regeneration of the alveolar bone 80 by removing mobility of the bone graft 82 filled in the deficient region.

Figure 12:
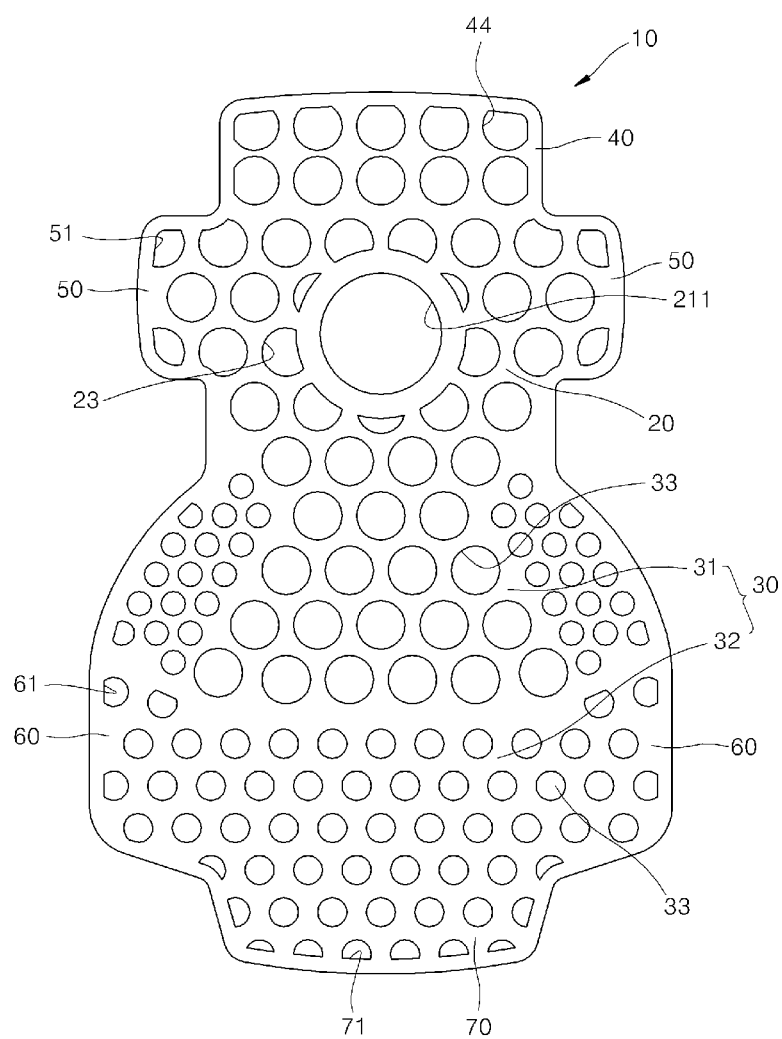
FIG. 12 is a plan view of a dental membrane according to an embodiment of the present invention.
Figure 13:
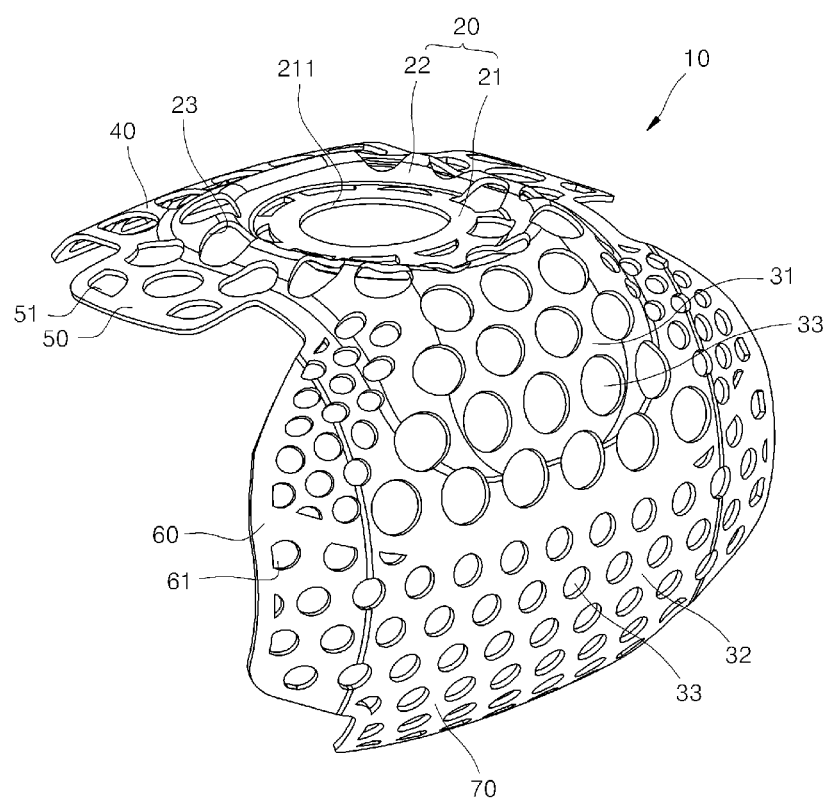
FIG. 13 is a perspective view of the dental membrane of FIG. 12 that is 3-dimensionally formed according to surgical conditions.
Figure 14:
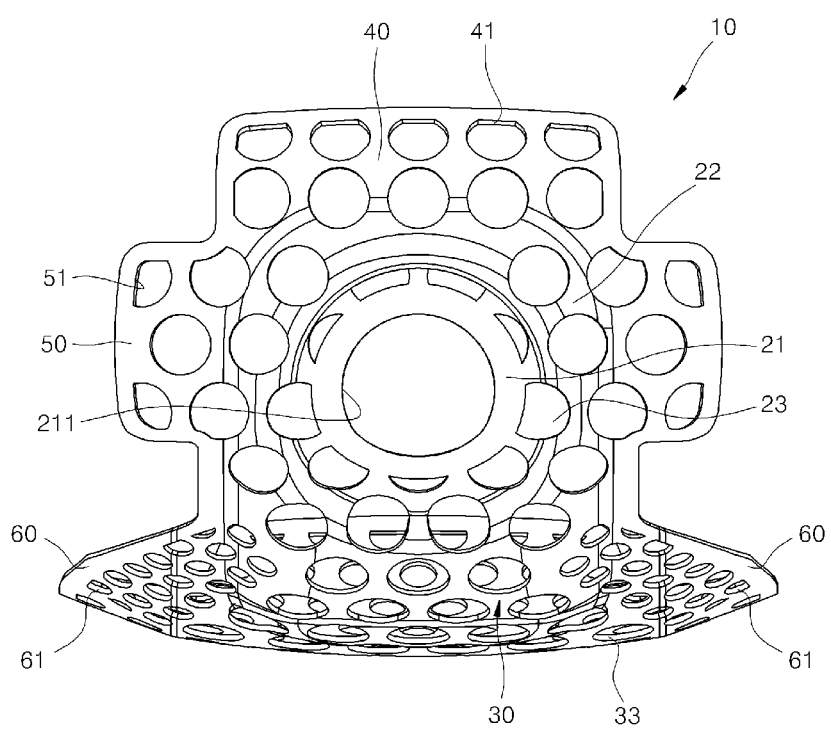
FIG. 14 is a plan view of FIG. 13.
Figure 15:
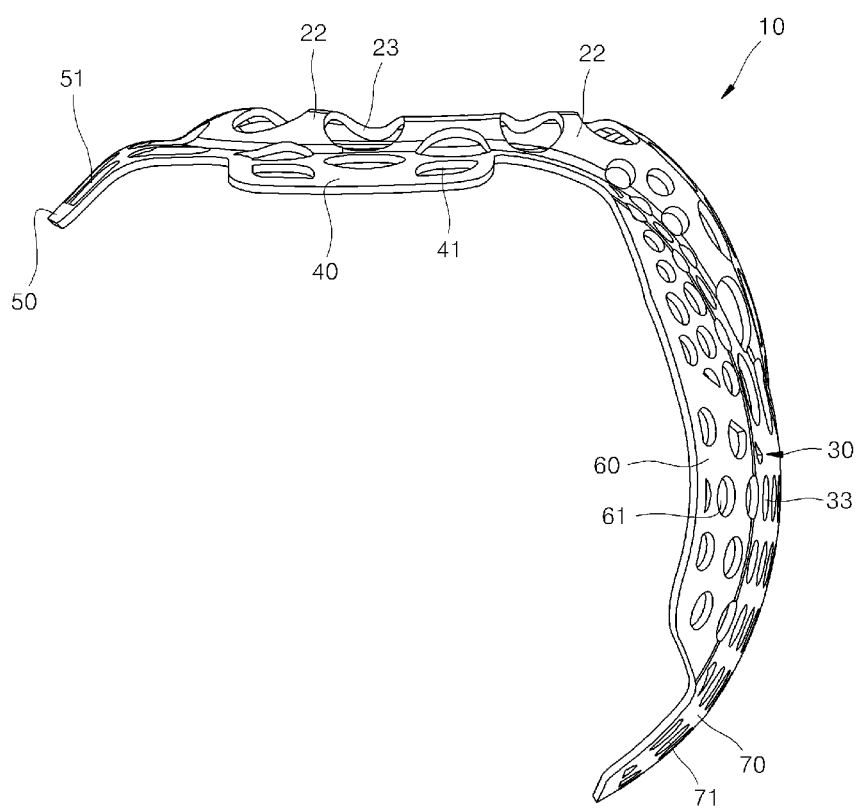
FIG. 15 is a lateral view of FIG. 14.

FIG. 12 is a two-dimensional plan view of the dental membrane 10, wherein a shape of the dental membrane 10 is trimmed according to a pre-classified bone deficient shape. FIGS. 13 through 15 illustrate the dental membrane 10, which is pre-trimmed for osteoanagenesis, bent in 3-dimensions by a predetermined bending device.

The dental membrane 10 according to the current embodiment is manufactured by pre-performing trimming and bending in three-dimensions by using a predetermined bending device instead of having an operator immediately perform trimming and bending according to a patient before a surgical procedure. Thus, the dental membrane 10 is pre-formed in a three-dimensional curved shape in a direction of the alveolar bone 80 to be regenerated according to a shape of the alveolar bone 80.

The dental membrane 10 includes an upper portion 20, a side bending portion 30, an upper extending portion 40, an upper wing portion 50, a side wing portion 60, and a side extending portion 70.

The upper portion 20 covers a top surface of a deficient region of the alveolar bone 80 where the bone graft 82 is filled in, and includes a center portion 21 and a papilla forming portion 22.

Here, the center portion 21 is disposed at a location corresponding to a location where an implant insert is inserted into, and is combined to the implant insert. The center portion 21 includes a center hole 211 through and into which the implant insert is penetrated and inserted.

The papilla forming portion 22 is disposed to surround at least a part of the center portion 21 and protrude upward from the center portion 21, and induces a papilla to be formed on the alveolar bone 80 to be regenerated. A cross-section of the papilla forming portion 22 generally has an arch shape. The papilla forming portion 22 is disposed adjacent to the center portion 21 in an overall ring shape to surround the center portion 21.

Figure 16:
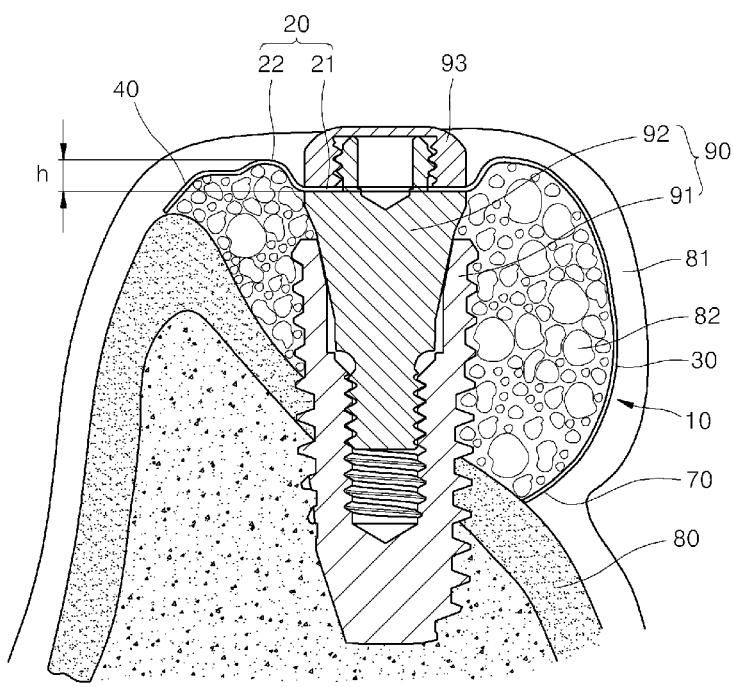
FIG. 16 is a view of the dental membrane of FIG. 13 installed to regenerate an alveolar bone, according to an embodiment of the present invention.

Here, referring to FIG. 16, a vertical distance h from the center portion 21 to an uppermost end of the papilla forming portion 22 may be in a range from about 0.1 mm to about 3 mm. If the vertical distance h is larger than the maximum, i.e., 3 mm, a generated papilla region of the alveolar bone 80 protrudes too much, and if the vertical distance h is smaller than the minimum, i.e., 0.1 mm, a height of a protruding region is low, and thus not only is an aesthetic sense low but also the protruding region may easily collapse after regeneration.

Also, the papilla forming portion 22 is spaced apart from the center portion 211 by a predetermined distance. In detail, a shortest distance between the center hole 211 and the papilla forming portion 22 may be in a range from 1 mm to 10 mm. Here, the shortest distance denotes a distance from a location of the center hole 211 nearest to the papilla forming portion 22 to a starting location of the papilla forming portion 22. As such, a papilla may be definitely formed, as the papilla forming portion 22 is spaced apart from the center portion 211 by the predetermined distance.

A plurality of first minute holes 23 are formed on the upper portion 20. The first minute hole 23 may be somewhat smaller than the center hole 211, and in detail, may have a size from 0.1 mm to 0.2 mm. The first minute holes 23 are used to activate a physiological reaction of blood between the bone graft 82 filled in the deficient region and surrounding osseous tissues such that osseous integration is stably and strongly performed between the bone graft 82 and the osseous tissues. The size of the first minute hole 23 is set as above such that blood is smoothly circulated.

The side bending portion 30 bends downward from the upper portion 20 to surround a side surface of the deficient region of the alveolar bone 80 where the bone graft 82 is filled in. The side bending portion 30 bends from the upper portion 20 to have a shape of "]", and has a plurality of second minute holes 33.

The side bending portion 30 includes a first bending portion 31 bending away from the upper portion 20, and a second bending portion 32 bending closer to the upper portion 20. Here, the second minute hole 33 of the first bending portion 31 may have a diameter from 0.8 mm to 2.0 mm, and the second minute hole 33 of the second bending portion 32 may have a diameter from 0.1 mm to 0.7 mm. Here, first minute holes at a lowermost end of the first bending portion 31 each have a crescent or half moon shape. In other words, the first minute holes at the lowermost end are arranged along a concave line. The first holes have a concave dish shape in correspondence with the concave line so that there is no local protrusion in some regions during bending by naturally forming a bending line. Also, the diameter of the second minute hole 33 of the second bending portion 32 is smaller than that of the first bending portion 31 so that the side bending portion 30 smoothly bends even when a radius of curvature is high, thus increasing flexibility during a bending process.

The upper extending portion 40 surrounds the bone graft 82 by extending from the upper portion 20, and in detail, bends downward by extending in a direction opposite to an extending direction of the side bending portion 30. A plurality of third minute holes 41 are formed on the upper extending portion 40, wherein osseous integration is increased as blood is circulated through the third minute holes 41. The upper extending portion 40 may be pre-formed three-dimensionally according to a final shape of the alveolar bone 80 to be regenerated.

The upper wing portion 50 extends and protrudes from two sides of the upper portion 20, and bends downward. In detail, the upper wing portion 50 bends downward to surround the bone graft 82. The upper wing portion 50 may protrude from a part of a side edge of the upper portion 20, and thus bending may be easily performed. In detail, the upper wing portion 50 covers an upper media or distal region of the alveolar bone 80. A plurality of fourth minute holes 51 are formed on the upper wing portion 50. By forming many minute holes, i.e., first through fourth minute holes 23, 33, 41, and 51, overall flexibility is increased and bending may be easily performed.

The side wing portion 60 bends inward by extending from two sides of the side bending portion 30. The bone graft 82 is prepared in the side wing portion 60, and the side wing portion 60 protrudes from two edges of the side bending portion 30 and bends towards the bone graft 82. The side wing portion 60 surrounds a buccal side of the deficient region, wherein a distance from the side bending portion 30 gradually increases from top to bottom and is uniformly maintained from the middle. The side wing portion 60 is integrally formed throughout a side surface of the side bending portion 30, and thus is easily detached from the deficient region after the osseous integration.

A plurality of fifth minute holes 61 are formed on the side wing portion 60, wherein a diameter of the fifth minute hole 61 may be smaller than that of the second minute hole 33. For example, the diameter of the fifth minute hole 61 may be from 0.1 mm to 0.7 mm. Also, the fifth minute holes 61 may be more closely arranged than the second minute holes 33, so that more holes are formed on the side wing portion 60 in a same area. In other words, a total area per unit area of the fifth minute holes 61 on the side wing portion 60 may be larger than that of the second minute holes 33 on the side bending portion 30. As such, by closely arranging the fifth minute holes 61 having a small size, overall flexibility of the side wing portion 60 may be increased and the side wing portion 60 may be easily taken out from the alveolar bone 80 without damaging the surroundings. Also, as the side wing portion 60 is flexible, bending may be easily performed.

The side extending portion 70 bends inward by extending from a bottom of the side bending portion 30. A plurality of sixth minute holes 71 are formed in the side extending portion 70. Here, a diameter of the sixth minute hole 71 may be smaller than that of the second minute hole 33, and thus sufficient flexibility may be obtained and the side extending portion 70 may be easily taken out from the alveolar bone 80 after osseous integration. Also, the sixth minute holes 71 prevent a surface of the side extending portion 70 from being sharpened during a trimming process, thereby preventing surrounding gingivae from being damaged.

Meanwhile, a tin coating layer or an anodizing coating layer may be formed on a surface of the dental membrane 10. In this case, the overall dental membrane 10 may seem black, thereby arousing an aesthetic sense.

The dental membrane 10 according to the current embodiment of the present invention has the following effects.

First, before attaching the dental membrane 10 to the alveolar bone 80, an implant insert 90 including a fixture 91 and an abutment 92 is inserted into the alveolar bone 80, and the bone graft 82 is filled in the deficient region. Then, the dental membrane 10 that is pre-formed in three-dimensions with respect to the implant insert 90 is combined to the implant insert 90. In detail, the implant insert 90 is inserted into the center hole 211 of the upper portion 20. After combining the dental membrane 10 to the implant insert 90 as such, the location of the dental membrane 10 is fixed to a top of the bone graft 82 by using a separate membrane fixing cover. Next, the dental membrane 10 is covered by gingivae 81, and the gingivae 81 are sutured. FIG. 16 shows the dental membrane 10 after the gingivae 81 are sutured. When the bone graft 82 is incorporated in the dental membrane 10 after a predetermined period of time, the sutured gingivae 81 are opened, and the dental membrane 10 is removed from the deficient region.

Meanwhile, the dental membrane 10 may include the papilla forming portion 22 so that a protruding region bulging upward may be formed on the alveolar bone 80 that is regenerated. Here, the gingivae 81 covering the dental membrane 10 may also protrude upward according to the shape of the alveolar bone 80 for an aesthetic sense.

As such, a dental membrane according to an embodiment of the present invention may form a papilla while an alveolar bone is regenerated, and thus an operator may avoid having to unnecessarily cut or delete an alveolar bone to form a papilla.

Also, since the dental membrane is customized and pre-formed in three-dimensions, the operator may only need to perform minimum trimming and bending at the spot of dental treatment during a surgical procedure, or the operator may not need to perform any trimming or bending at all. In particular, since the dental membrane has a pre-customized shape and is not locally bent, the dental membrane may be formed without any protruding region, and a puckering phenomenon (for example, a creasing and wrinkling phenomenon) that can typically occur during bending of the dental membrane at the spot of the dental treatment may be prevented. As a result, the dental membrane may be prevented from locally protruding at the spot of the dental treatment, and a separate locking screw may not be required while locking the dental membrane to an implant insert.

Also, by varying sizes of minute holes according to regions to increase flexibility of a region that is to be largely bent, bendability may be increased. Accordingly, spot workability may be increased even when local bending of the dental membrane is required at the spot of the dental treatment.

Also, by configuring a side wing portion to have high flexibility, not only is bendability increased, but also the dental membrane may be easily removed from a bone graft.

A dental membrane according to an embodiment of the present invention may be modified as follows.

Figure 17:
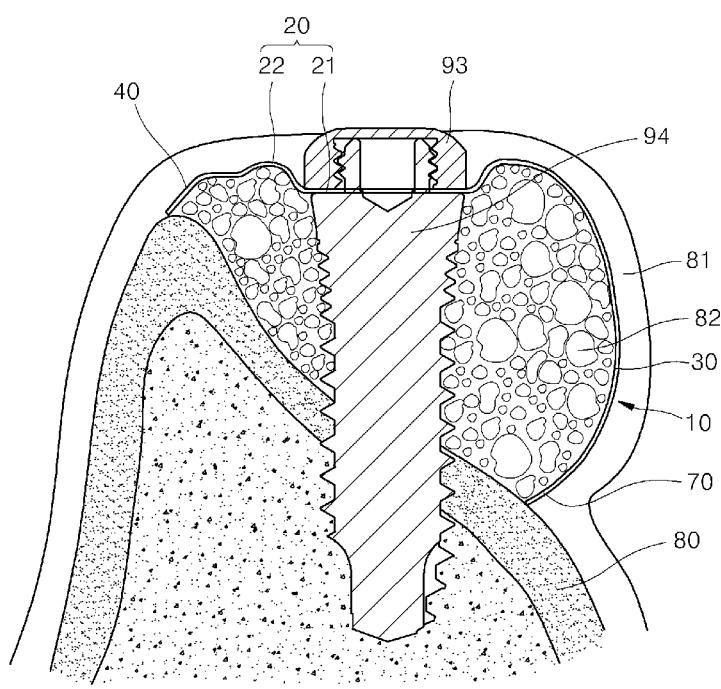
FIG. 17 is a view of the dental membrane of FIG. 13 installed to regenerate an alveolar bone, according to another embodiment of the present invention.

First, in FIG. 16, the implant insert 90 includes the fixture 91 and the abutment 92, but alternatively, an implant insert 94 may include an abutment integrated fixture as shown in FIG. 17, wherein the fixture 91 and the abutment 92 are integrated with each other. Here, a center hole of a dental membrane is combined to a top of the abutment integrated fixture. Alternatively, although not illustrated, the implant insert 90 may only include a fixture.

Figure 18:
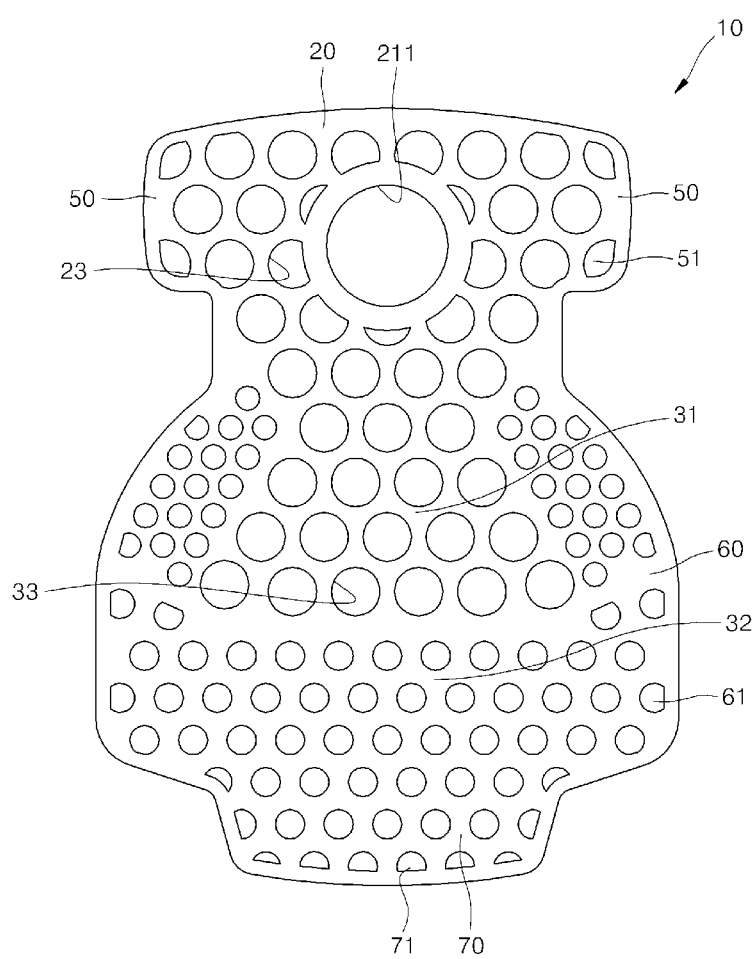
FIG. 18 is a plan view of a dental membrane according to another embodiment of the present invention.
Figure 19:
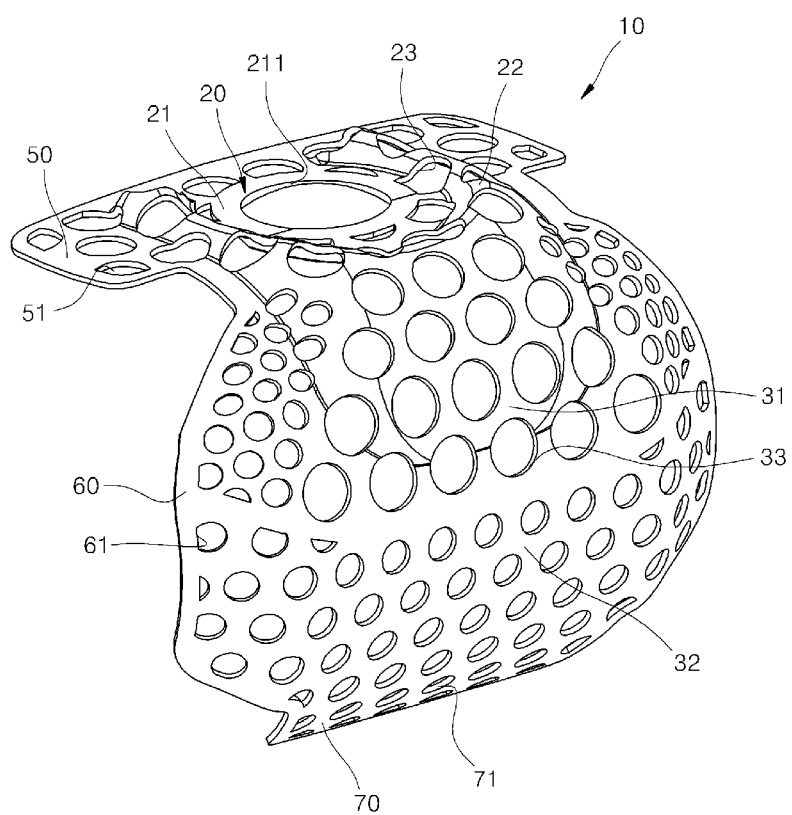
FIG. 19 is a view of the dental membrane of FIG. 18 that is 3-dimensionally formed.
Figure 20:
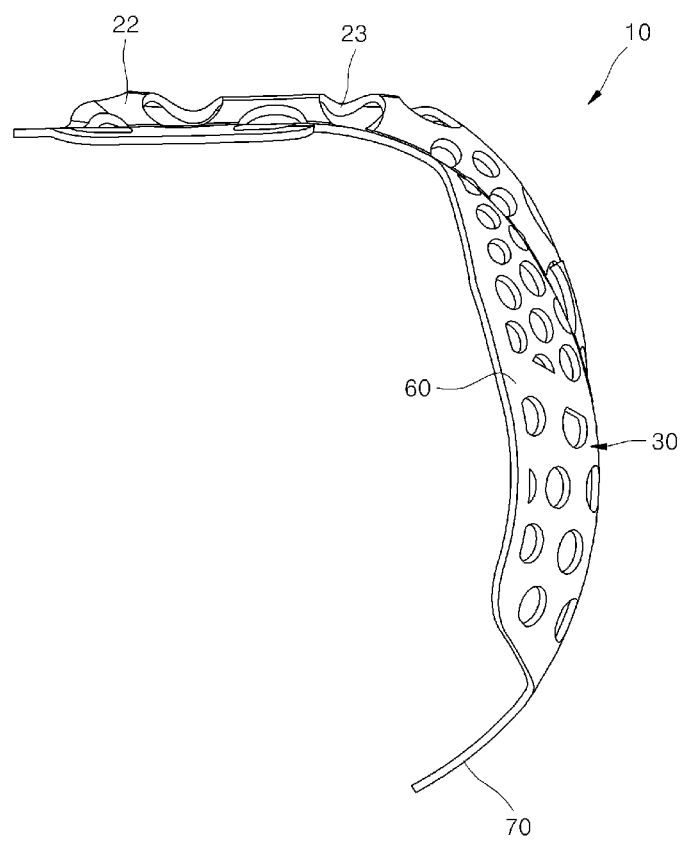
FIG. 20 is a lateral view of FIG. 19.

Also, in the above embodiment, the dental membrane 10 includes the upper portion 20, the side bending portion 30, the upper extending portion 40, the upper wing portion 50, the side wing portion 60, and the side extending portion 70, but as shown in FIGS. 18 through 20, the dental membrane 10 may include only the upper portion 20, the side bending portion 30, the upper wing portion 50, the side wing portion 60, and the side extending portion 70, without the upper extending portion 40. The dental membrane 10 shown in FIGS. 18 through 20 is usable when a deficient region of an alveolar bone is on a same level as a top surface of the dental membrane 10.

Figure 21:
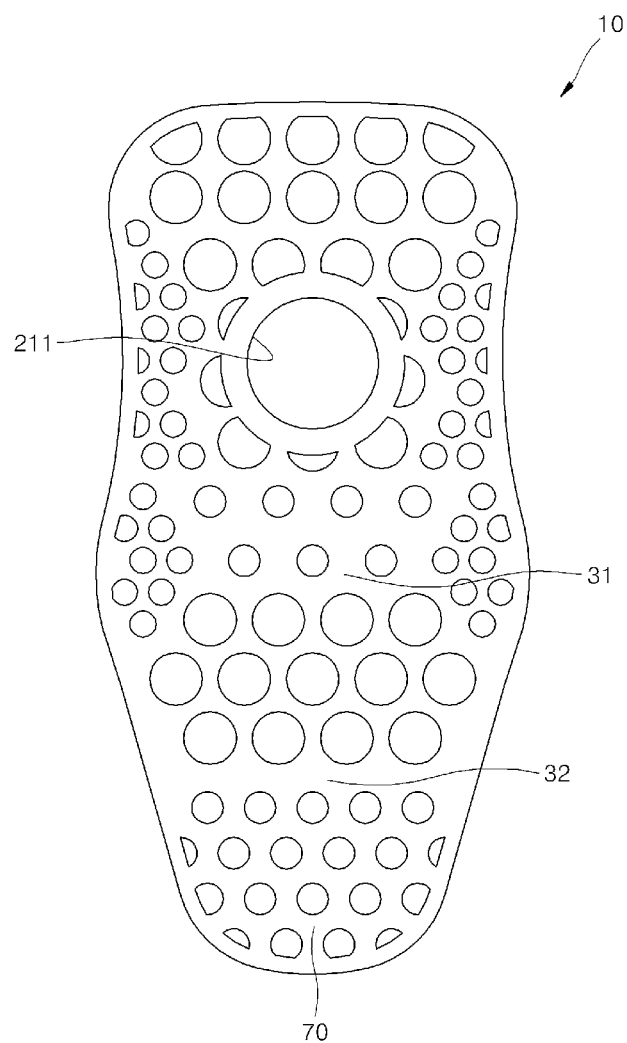
FIG. 21 is a plan view of a dental membrane according to another embodiment of the present invention.
Figure 22:
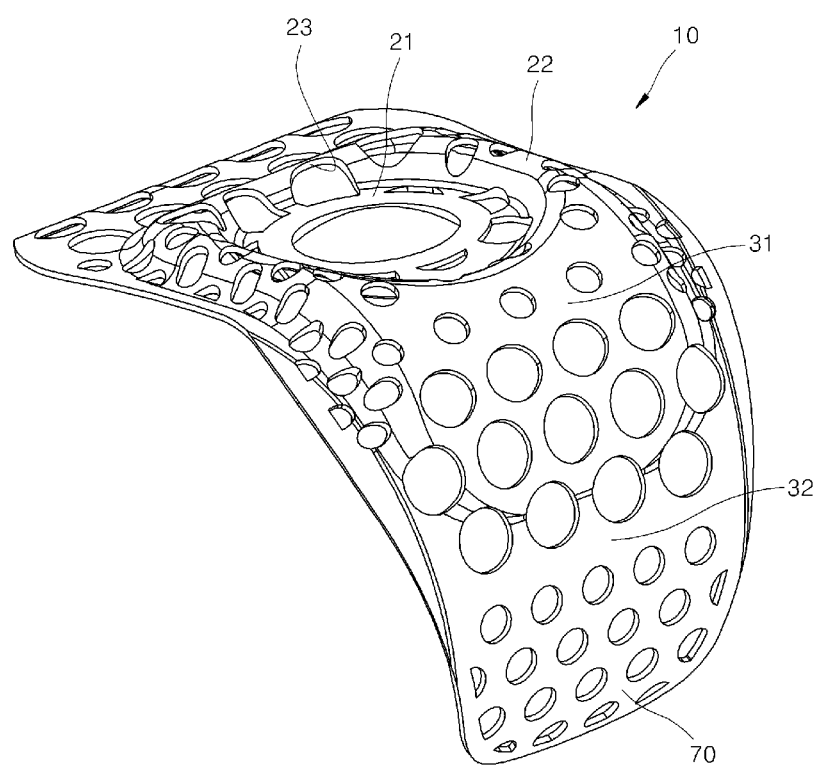
FIG. 22 is a view of the dental membrane of FIG. 21 that is 3-dimensionally formed.
Figure 23:
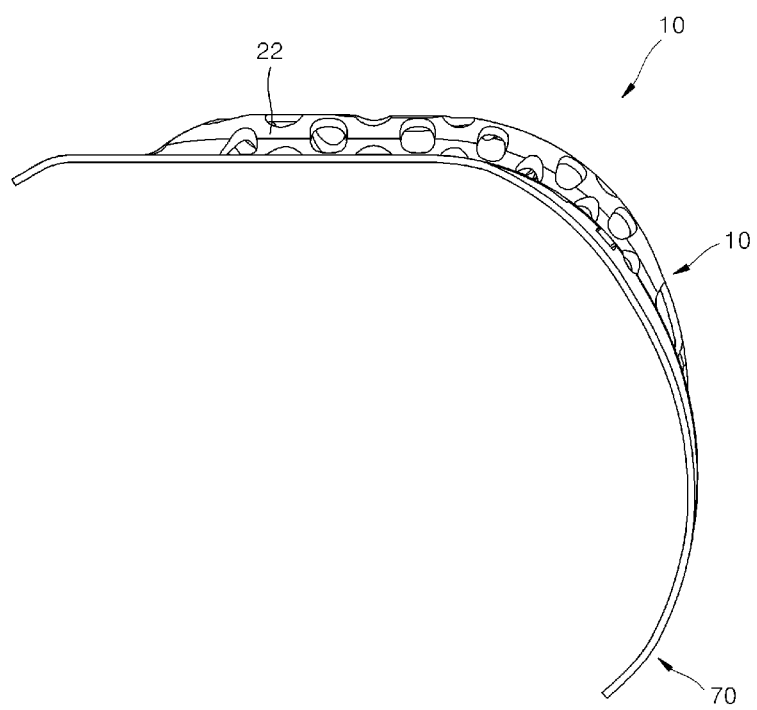
FIG. 23 is a lateral view of FIG. 22.

Also, the dental membrane 10 of FIGS. 18 through 20 includes the upper portion 20, the side bending portion 30, the upper wing portion 50, the side wing portion 60, and the side extending portion 70. Alternatively, the upper wing portion 50 may not be separately prepared at the upper portion 20, but rather the upper portion 20 may have a quadrangular flat shape such that a width of the upper portion 20 is expanded to cover an overall top surface of an alveolar bone as shown in FIGS. 21 through 23. Alternatively, the dental membrane 10 may only include the side bending portion 30 even without the side wing portion 60.

Figure 24:
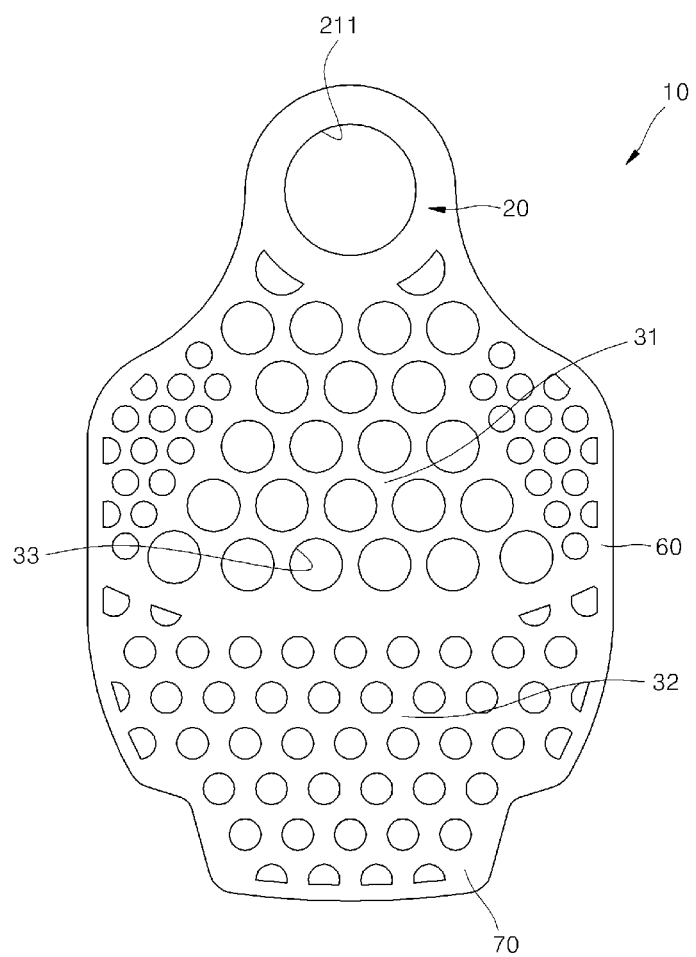
FIG. 24 is a plan view of a dental membrane according to another embodiment of the present invention.
Figure 25:
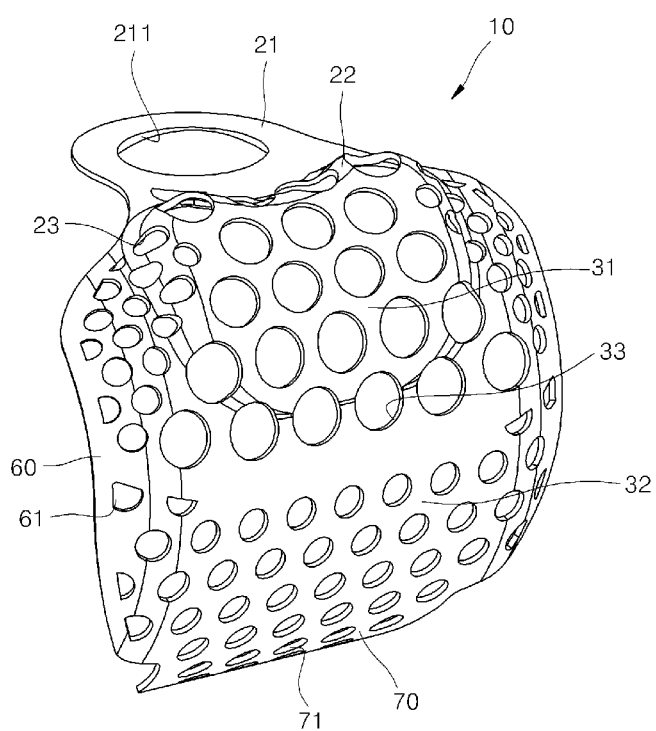
FIG. 25 is a view of the dental membrane of FIG. 24 that is 3-dimensionally formed.
Figure 26:
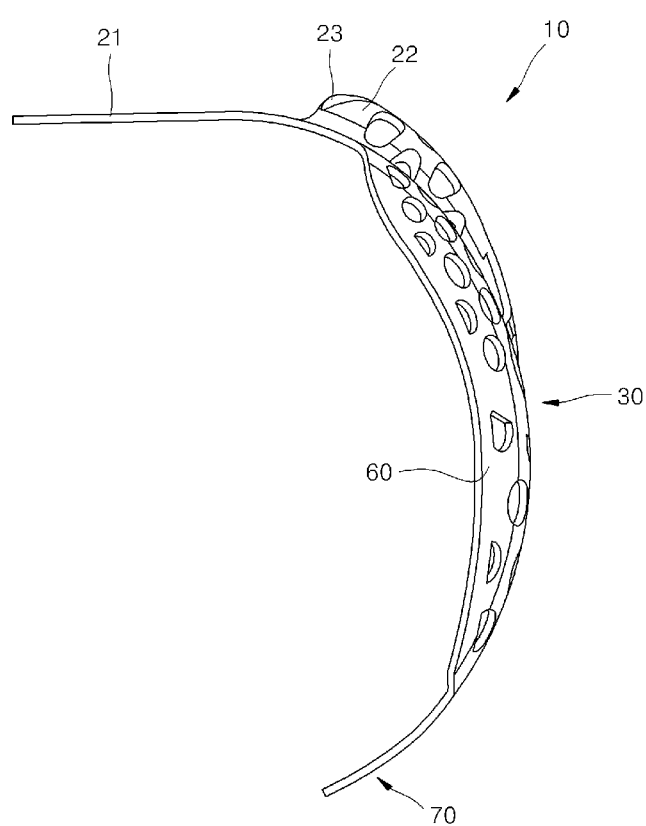
FIG. 26 is a lateral view of FIG. 25.

Also, the dental membrane 10 of FIGS. 18 through 20 includes the upper portion 20, the side bending portion 30, the upper wing portion 50, the side wing portion 60, and the side extending portion 70, but alternatively, the dental membrane 10 may only include the upper portion 20, the side bending portion 30, the side wing portion 60, and the side extending portion 70 as shown in FIGS. 24 through 26. Here, a papilla forming portion 22 of the upper portion 20 does not have a ring shape, and instead it locally protrudes towards a lip side. The dental membrane 10 of FIGS. 24 through 26 may mainly be used when a deficient region of an alveolar bone is limited to one side.

Figure 27:
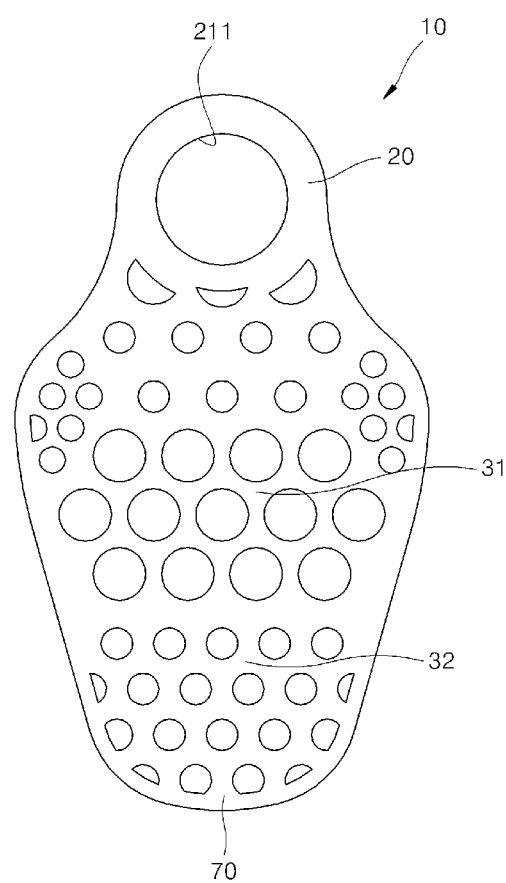
FIG. 27 is a plan view of a dental membrane according to another embodiment of the present invention.
Figure 28:
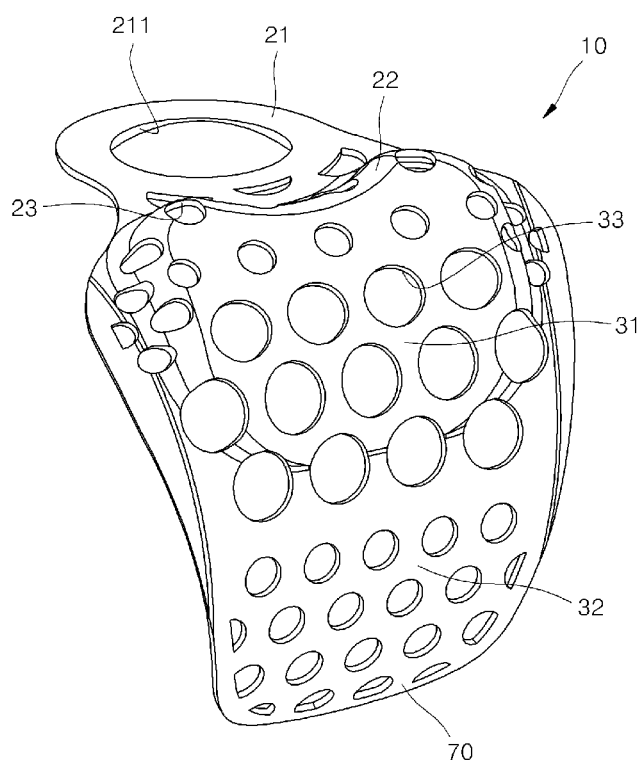
FIG. 28 is a view of the dental membrane of FIG. 27 that is 3-dimensionally formed.
Figure 29:
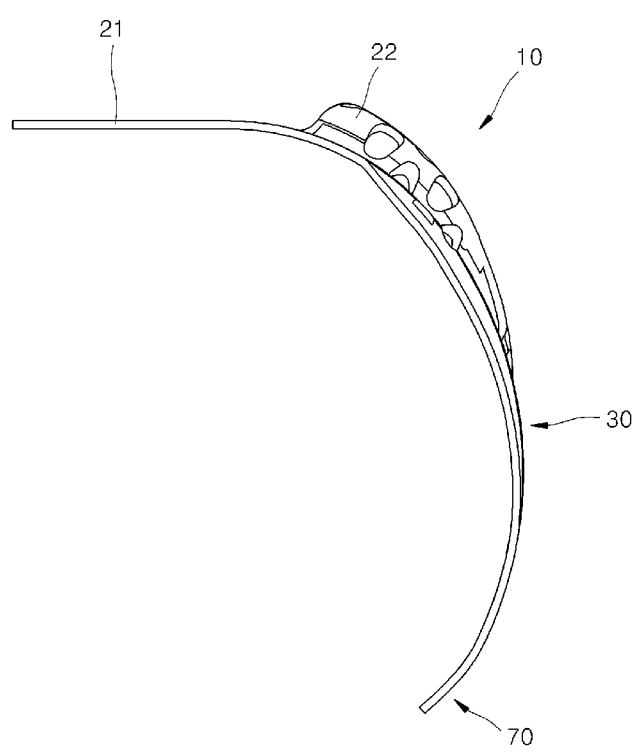
FIG. 29 is a lateral view of FIG. 28.

Also, the dental membrane 10 of FIGS. 24 through 26 includes the upper portion 20, the side bending portion 30, the side wing portion 60, and the side extending portion 70, but alternatively, the dental membrane 10 may include the upper portion 20, the side bending portion 30, and the side extending portion 70 as shown in FIGS. 27 through 29. The dental membrane 10 of FIGS. 27 through 29 may also be mainly used when a deficient region of an alveolar bone is limited to one side.

Figure 30:
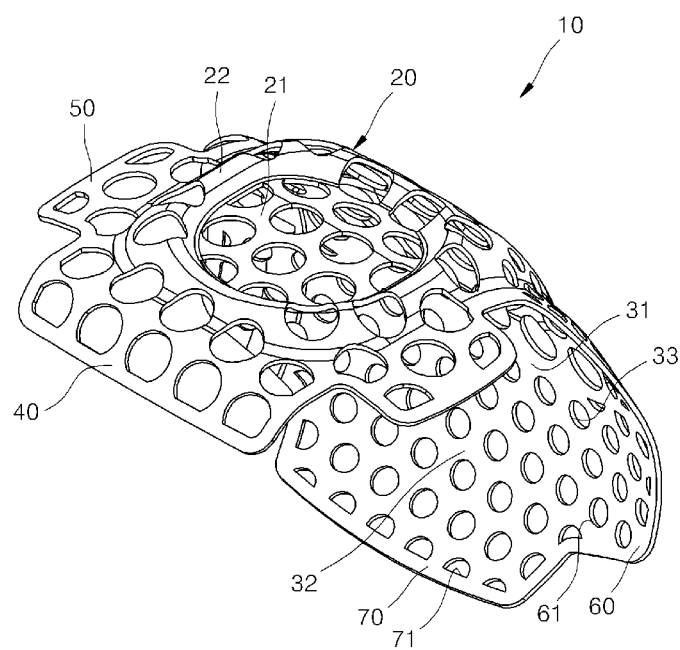
FIG. 30 is a perspective view of a dental membrane according to another embodiment of the present invention.
Figure 31:
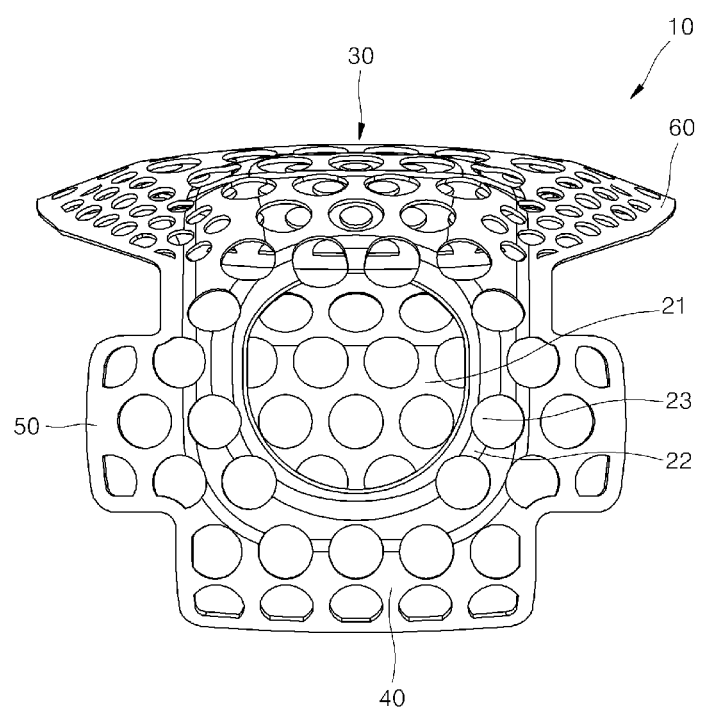
FIG. 31 is a plan view of FIG. 30.

Also, according to the dental membrane 10 of FIGS. 12 through 15, a center hole is formed in the upper portion 20, but alternatively, a plurality of first minute holes 23 may be formed without a center hole as shown in FIGS. 30 and 31. In other words, only a center hole may not be formed while the upper portion 20, the side bending portion 30, the upper extending portion 40, the upper wing portion 50, the side wing portion 60, and the side extending portion 70 are prepared. Here, the dental membrane 10 may be fixed by using a plurality of fixing screws disposed on an edge of the dental membrane 10. Here, the fixing screws have small screw shapes and may be disposed on two ends of the upper extending portion 40 and two ends of the side extending portion 70.

Figure 32:
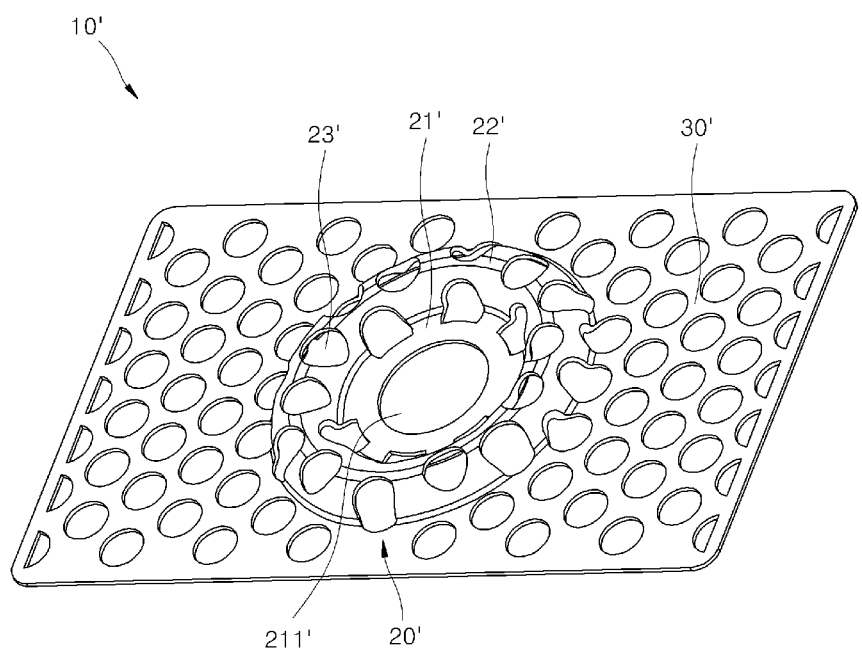
FIG. 32 is a perspective view of a dental membrane according to another embodiment of the present invention.
Figure 33:
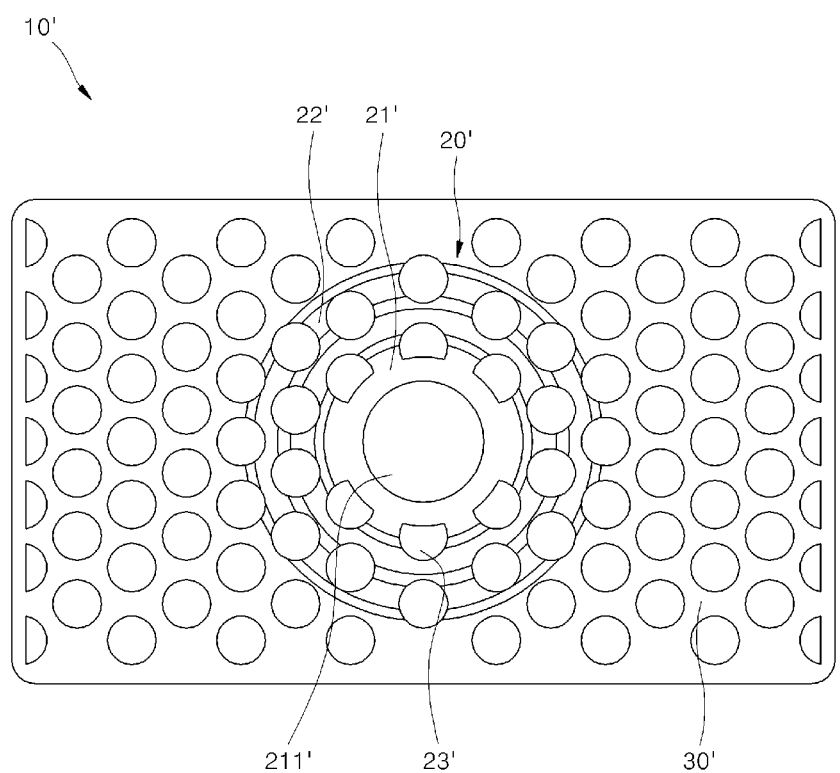
FIG. 33 is a plan view of FIG. 32.
Figure 34:
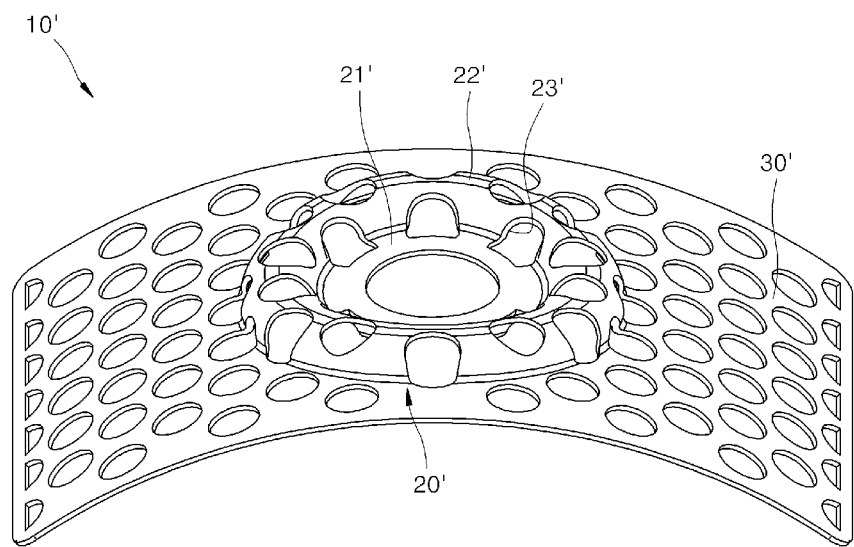
FIG. 34 is a perspective view of a dental membrane according to another embodiment of the present invention.
Figure 35:
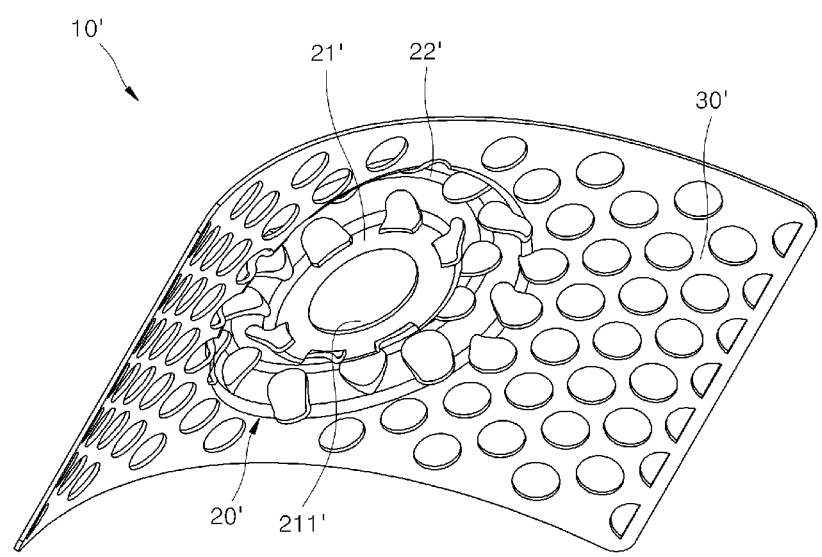
FIG. 35 is a perspective view of FIG. 34 from another direction.

Alternatively, as shown in FIGS. 32 and 33, a dental membrane 10' may include an upper portion 20' surrounding a top surface of a deficient region of an alveolar bone where a bone graft is filled in, and a horizontal extending portion 30' horizontally extending from the upper portion 20'. The upper portion 20' may include a center portion 21' disposed at a location corresponding to a location where an implant insert is inserted into and having a center hole 211' combined to the implant insert, and a papilla forming portion 22' surrounding at least a part of the center portion 21' and protruding upward from the center portion 21'. As a result, a papilla may be induced to protrude upward from the alveolar bone to be regenerated. In other words, the dental membrane 10' may have an overall quadrangular flat shape unlike the previous embodiments, wherein the papilla forming portion 22' is prepared around the center portion 21'.

The dental membrane 10' of FIGS. 32 and 33 may be used to regenerate an alveolar bone without separate bending or trimming on the spot of a dental treatment, but may alternatively be bent or trimmed to a predetermined shape if required.

Also, the dental membrane 10' may be bent to a predetermined shape, unlike the example shown in FIGS. 32 and 33. In other words, the horizontal extending portion 30' may be bent downward so that the dental membrane 10' has an overall curved shape.

Figure 36:
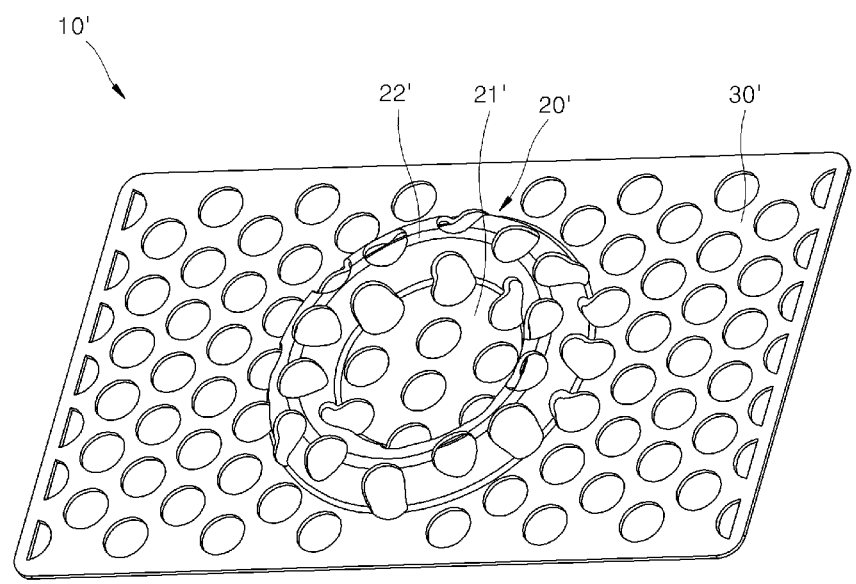
FIG. 36 is a perspective view of a dental membrane according to another embodiment of the present invention.

Alternatively, as shown in FIG. 36, the dental membrane 10' may include the upper portion 20' surrounding the top surface of the deficient region of the alveolar bone where the bone graft is filled in, and the horizontal extending portion 30' horizontally extending from the upper portion 20'. The upper portion 20' may include the center portion 21' having a plurality of minute holes, and the papilla forming portion 22' surrounding at least a part of the center portion 21' and protruding upward from the center portion 21'. As a result, a papilla may be induced to protrude upward on the alveolar bone to be regenerated. In other words, unlike FIGS. 32 and 33, the dental membrane 10' of FIG. 36 may not include the center hole 211'. Here, the dental membrane 10' may be fixed to the alveolar bone by a plurality of fixing screws disposed on edge corners of the dental membrane 10'.

Figure 37:
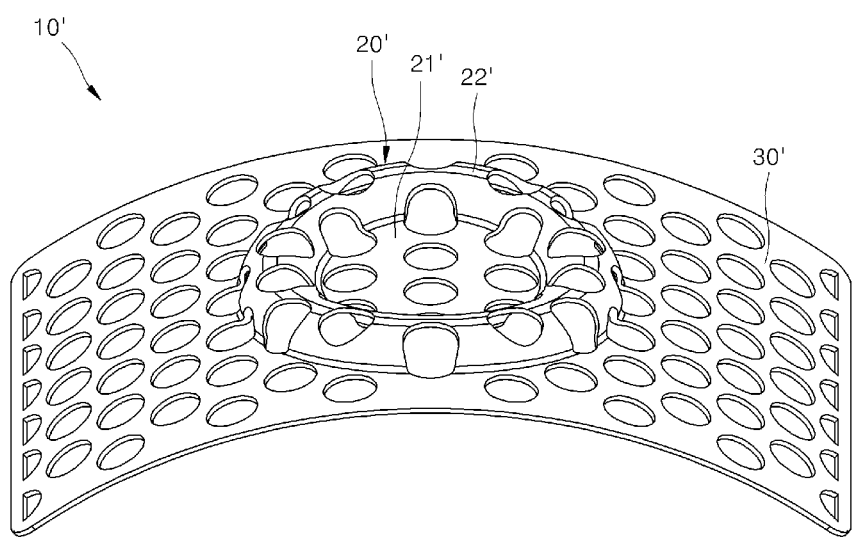
FIG. 37 is a perspective view of a dental membrane according to another embodiment of the present invention.

Alternatively, the dental membrane 10' may be bent in a predetermined shape as shown in FIG. 37. In other words, the horizontal extending portion 30' may be bent downward in an overall curved shape.

The invention claimed is:

1. A dental membrane for being disposed in a deficient region of an alveolar bone to form a space for regeneration of the alveolar bone or to surround a bone graft, wherein the dental membrane includes an insert for being inserted and fixed in the alveolar bone and a cover member that is combined to the insert, the dental membrane comprising:
an upper portion for surrounding a top surface of the deficient region of the alveolar bone; and
a side bending portion bended downward from the upper portion for surrounding a side surface of the deficient region of the alveolar bone,
wherein the upper portion comprises:
a combined portion combined to the insert and the cover member, wherein the combined portion is fixed to the insert and the cover member; and
a protruding portion extending and protruding upward from the combined portion, wherein the protruding portion surrounds at least a part of a side surface of the cover member.

2. The dental membrane of claim 1, wherein the combined portion is ring shaped, has a center, and has a through hole at the center.

3. The dental membrane of claim 1, wherein the protruding portion has a shape corresponding to an outer shape of the cover member.

4. The dental membrane of claim 3, wherein the protruding portion contacts a side surface of the cover member.

5. The dental membrane of claim 3, wherein the protruding portion is spaced apart from the side surface of the cover member.

6. The dental membrane of claim 1, wherein an uppermost end of the protruding portion is disposed on a same location as a top surface of the cover member.

7. The dental membrane of claim 1, wherein the protruding portion protrudes from the combined portion in a range from 0.1 mm to 5 mm.

8. The dental membrane of claim 1, wherein the protruding portion has a cylindrical shape.

9. The dental membrane of claim 1, wherein at least one hole is formed in the protruding portion.

10. The dental membrane of claim 1, wherein the protruding portion comprises:
a first extending portion connected to the combined portion and extending upward; and
a second extending portion horizontally extending from the first extending portion.

11. The dental membrane of claim 1, wherein the dental membrane comprises two side bending portions that are respectively disposed on two sides of the upper portion.

12. A dental membrane for being disposed in a deficient region of an alveolar bone to form a space for regeneration of the alveolar bone or to surround a bone graft, wherein the dental membrane includes an insert for being inserted and fixed in the alveolar bone and a cover member that is combined to the insert, the dental membrane comprising:
an upper portion for surrounding a top surface of the deficient region and comprising a combined portion fixed by contacting the insert and a protruding portion extending and protruding upward from the combined portion; and
a side bending portion bending downward from the upper portion,
wherein the protruding portion surrounds at least a part of a side surface of the cover member.

13. The dental membrane of claim 12, wherein the combined portion is ring shaped, has a center, and has a through hole at the center.

14. The dental membrane of claim 12, wherein the protruding portion has a shape corresponding to an outer shape of the cover member.

15. The dental membrane of claim 14, wherein the protruding portion contacts a side surface of the cover member.

16. The dental membrane of claim 14, wherein the protruding portion is spaced apart from the side surface of the cover member.

17. The dental membrane of claim 12, wherein an uppermost end of the protruding portion is disposed on a same location as a top surface of the cover member.

18. The dental membrane of claim 12, wherein the protruding portion protrudes from the combined portion in a range from 0.1 mm to 5 mm.

19. The dental membrane of claim 12, wherein at least one hole is formed in the protruding portion.

20. The dental membrane of claim 12, wherein the protruding portion comprises:
 a first extending portion connected to the combined portion and extending upward; and
 a second extending portion horizontally extending from the first extending portion.

21. The dental membrane of claim 12, wherein the dental membrane comprises two side extending portions that are respectively disposed on two sides of the upper portion.

22. The dental membrane of claim 21, wherein at least one of the side extending portions is bendable downward from the upper portion.

* * * * *